(12) United States Patent
Browning

(10) Patent No.: US 10,682,213 B2
(45) Date of Patent: *Jun. 16, 2020

(54) SURGICAL IMPLANT CONSISTING OF NON-ABSORBABLE MATERIAL

(71) Applicant: Coloplast A/S, Humlebaek (DK)

(72) Inventor: James Browning, Glasgow (GB)

(73) Assignee: Coloplast A/S, Humlebaek (DK)

( * ) Notice: Subject to any disclaimer, the term of this patent is extended or adjusted under 35 U.S.C. 154(b) by 216 days.

This patent is subject to a terminal disclaimer.

(21) Appl. No.: 15/913,937

(22) Filed: Mar. 7, 2018

(65) Prior Publication Data
US 2018/0200037 A1    Jul. 19, 2018

Related U.S. Application Data

(63) Continuation of application No. 14/972,133, filed on Dec. 17, 2015, now Pat. No. 9,943,390, which is a (Continued)

(30) Foreign Application Priority Data

Mar. 30, 2001    (GB) .................................. 0108088.6

(51) Int. Cl.
*A61F 2/02*    (2006.01)
*A61B 17/08*    (2006.01)
*A61F 2/00*    (2006.01)

(52) U.S. Cl.
CPC .......... *A61F 2/0036* (2013.01); *A61F 2/0063* (2013.01); *A61F 2002/0068* (2013.01); (Continued)

(58) Field of Classification Search
CPC ...... A61F 2002/0068; A61F 2250/0071; A61F 2/0036; A61F 2/0063
See application file for complete search history.

(56) References Cited

U.S. PATENT DOCUMENTS

| 1,450,101 A | 3/1923 | Mathewson |
| 2,097,018 A | 10/1937 | Chamberlin |

(Continued)

FOREIGN PATENT DOCUMENTS

| CA | 2592617 C | 2/2004 |
| DE | 2305815 A1 | 8/1974 |

(Continued)

OTHER PUBLICATIONS

Parra and Shaker, "Experience with a Simplified Technique for the Treatment of Female Stress Urinary Incontinence," British Journal of Urology, 1990, 66:615-617.

(Continued)

*Primary Examiner* — Julian W Woo
(74) *Attorney, Agent, or Firm* — Coloplast Corp., Coloplast A/S; Nick Baumann

(57) ABSTRACT

A surgical implant is provided for implantation into a body of a patient to treat a vaginal prolapse in the patient. The surgical implant is made of non-absorbable material and includes a knitted mesh having a mass density of less than 25 g/m². The knitted mesh includes polypropylene strands having a diameter of less than about 600 μm, major spaces located between adjacent ones of the strands, the major spaces having a width of from about 1 mm to 10 mm, and pores located within the strands, the pores having a diameter of from about 50 μm to 200 μm. The knitted mesh is secured in place to treat the prolapse.

11 Claims, 10 Drawing Sheets

Related U.S. Application Data continuation of application No. 13/316,507, filed on Dec. 11, 2011, now Pat. No. 9,248,011, which is a continuation of application No. 12/551,676, filed on Sep. 1, 2009, now Pat. No. 8,100,924, which is a continuation of application No. 10/473,825, filed as application No. PCT/GB02/01234 on Apr. 2, 2002, now Pat. No. 7,594,921.

(52) U.S. Cl.
CPC .......... *A61F 2002/0072* (2013.01); *A61F 2002/0081* (2013.01); *A61F 2002/0086* (2013.01); *A61F 2250/0071* (2013.01)

(56) References Cited

U.S. PATENT DOCUMENTS

| | | |
|---|---|---|
| 2,427,176 A | 9/1947 | Aldeen |
| 2,738,790 A | 3/1956 | Todt, Sr. et al. |
| 3,054,406 A | 9/1962 | Usher |
| 3,124,136 A | 3/1964 | Usher |
| 3,126,600 A | 3/1964 | De Marre |
| 3,182,662 A | 5/1965 | Shirodkar |
| 3,311,110 A | 3/1967 | Sol Singerman et al. |
| 3,384,073 A | 5/1968 | Van Winkle, Jr. |
| 3,472,232 A | 10/1969 | Pendleton |
| 3,580,313 A | 5/1971 | McKnight |
| 3,763,860 A | 10/1973 | Clarke |
| 3,789,828 A | 2/1974 | Schulte |
| 3,858,783 A | 1/1975 | Kapitanov et al. |
| 3,888,975 A | 6/1975 | Ramwell |
| 3,911,911 A | 10/1975 | Scommegna |
| 3,913,179 A | 10/1975 | Rhee |
| 3,913,573 A | 10/1975 | Gutnick |
| 3,916,899 A | 11/1975 | Theeuwes et al. |
| 3,924,633 A | 12/1975 | Cook et al. |
| 3,993,058 A | 11/1976 | Hoff |
| 3,995,619 A | 12/1976 | Glatzer |
| 4,019,499 A | 4/1977 | Fitzgerald |
| 4,037,603 A | 7/1977 | Wendorff |
| 4,128,100 A | 12/1978 | Wendorff |
| 4,172,458 A | 10/1979 | Pereyra |
| 4,233,968 A | 11/1980 | Shaw, Jr. |
| 4,235,238 A | 11/1980 | Ogiu et al. |
| 4,246,660 A | 1/1981 | Wevers |
| 4,409,866 A | 10/1983 | McBride |
| 4,441,497 A | 4/1984 | Paudler |
| 4,444,933 A | 4/1984 | Columbus et al. |
| 4,452,245 A | 6/1984 | Usher |
| 4,509,516 A | 4/1985 | Richmond |
| 4,632,100 A | 12/1986 | Somers et al. |
| 4,633,873 A | 1/1987 | Dumican et al. |
| 4,646,731 A | 3/1987 | Brower |
| 4,655,221 A | 4/1987 | Devereux |
| 4,769,038 A | 9/1988 | Bendavid et al. |
| 4,775,380 A | 10/1988 | Seedhom et al. |
| 4,784,139 A | 11/1988 | Demos |
| 4,799,484 A | 1/1989 | Smith et al. |
| 4,857,041 A | 8/1989 | Annis et al. |
| 4,865,031 A | 9/1989 | O'Keeffe |
| 4,873,976 A | 10/1989 | Schreiber |
| 4,911,164 A | 3/1990 | Roth |
| 4,920,986 A | 5/1990 | Biswas |
| 4,938,760 A | 7/1990 | Burton et al. |
| 5,004,468 A | 4/1991 | Atkinson |
| 5,013,292 A | 5/1991 | Lemay |
| 5,053,043 A | 10/1991 | Gottesman et al. |
| 5,085,661 A | 2/1992 | Moss |
| 5,112,344 A | 5/1992 | Petros |
| 5,123,428 A | 6/1992 | Schwarz |
| 5,123,910 A | 6/1992 | McIntosh |
| 5,149,329 A | 9/1992 | Richardson |
| 5,188,636 A | 2/1993 | Fedotov |
| 5,207,694 A | 5/1993 | Broome |
| 5,209,756 A | 5/1993 | Seedhom et al. |
| 5,219,352 A | 6/1993 | Atkinson |
| 5,234,436 A | 8/1993 | Eaton et al. |
| 5,250,033 A | 10/1993 | Evans et al. |
| 5,256,133 A | 10/1993 | Spitz |
| 5,259,835 A | 11/1993 | Clark et al. |
| 5,281,237 A | 1/1994 | Gimpelson |
| 5,306,279 A | 4/1994 | Atkinson |
| 5,328,077 A | 7/1994 | Lou |
| 5,336,239 A | 8/1994 | Gimpelson |
| 5,337,736 A | 8/1994 | Reddy |
| 5,342,376 A | 8/1994 | Ruff |
| 5,356,432 A | 10/1994 | Rutkow et al. |
| 5,362,294 A | 11/1994 | Seitzinger |
| 5,368,595 A | 11/1994 | Lewis |
| 5,383,904 A | 1/1995 | Totakura et al. |
| 5,386,836 A | 2/1995 | Biswas |
| 5,397,353 A | 3/1995 | Oliver et al. |
| 5,403,328 A | 4/1995 | Shallman |
| 5,405,360 A | 4/1995 | Tovey |
| 5,413,598 A | 5/1995 | Moreland |
| 5,434,146 A | 7/1995 | Labrie et al. |
| 5,439,467 A | 8/1995 | Benderev et al. |
| 5,456,711 A | 10/1995 | Hudson |
| 5,473,796 A | 12/1995 | Fusillo |
| 5,474,543 A | 12/1995 | McKay |
| 5,486,197 A | 1/1996 | Le et al. |
| 5,507,754 A | 4/1996 | Green et al. |
| 5,507,796 A | 4/1996 | Hasson |
| 5,520,700 A | 5/1996 | Beyar et al. |
| 5,522,896 A | 6/1996 | Prescott |
| 5,544,664 A | 8/1996 | Benderev et al. |
| 5,549,619 A | 8/1996 | Peters et al. |
| 5,562,685 A | 10/1996 | Mollenauer et al. |
| 5,562,689 A | 10/1996 | Green et al. |
| 5,569,273 A | 10/1996 | Titone et al. |
| 5,571,139 A | 11/1996 | Jenkins, Jr. |
| 5,591,163 A | 1/1997 | Thompson |
| 5,611,515 A | 3/1997 | Benderev et al. |
| 5,628,756 A | 5/1997 | Barker, Jr. et al. |
| 5,633,286 A | 5/1997 | Chen |
| 5,645,568 A | 7/1997 | Chervitz et al. |
| 5,647,836 A | 7/1997 | Blake, III et al. |
| 5,655,270 A | 8/1997 | Boisvert |
| 5,669,935 A | 9/1997 | Rosenman et al. |
| 5,683,349 A | 11/1997 | Makower et al. |
| 5,689,860 A | 11/1997 | Matoba et al. |
| 5,693,072 A | 12/1997 | McIntosh |
| 5,695,525 A | 12/1997 | Mulhauser et al. |
| 5,697,931 A | 12/1997 | Thompson |
| 5,697,978 A | 12/1997 | Sgro |
| 5,720,766 A | 2/1998 | Zang et al. |
| 5,749,884 A | 5/1998 | Benderev et al. |
| 5,766,221 A | 6/1998 | Benderev et al. |
| 5,774,994 A | 7/1998 | Stein et al. |
| 5,807,403 A | 9/1998 | Beyar et al. |
| 5,816,258 A | 10/1998 | Jervis |
| 5,830,220 A | 11/1998 | Wan et al. |
| 5,836,314 A | 11/1998 | Benderev et al. |
| 5,836,315 A | 11/1998 | Benderev et al. |
| 5,840,011 A | 11/1998 | Landgrebe et al. |
| 5,842,478 A | 12/1998 | Benderev et al. |
| 5,851,229 A | 12/1998 | Lentz et al. |
| 5,860,425 A | 1/1999 | Benderev et al. |
| 5,899,909 A | 5/1999 | Claren et al. |
| 5,904,692 A | 5/1999 | Steckel et al. |
| 5,919,232 A | 7/1999 | Chaffringeon et al. |
| 5,922,026 A | 7/1999 | Chin |
| 5,934,283 A | 8/1999 | Willem et al. |
| 5,935,122 A | 8/1999 | Fourkas et al. |
| 5,944,732 A | 8/1999 | Raulerson et al. |
| 5,954,057 A | 9/1999 | Li |
| 5,971,967 A | 10/1999 | Willard |
| 5,972,000 A | 10/1999 | Beyar et al. |
| 5,988,171 A | 11/1999 | Sohn et al. |
| 5,990,378 A | 11/1999 | Ellis |
| 5,997,554 A | 12/1999 | Thompson |
| 6,005,191 A | 12/1999 | Tzeng et al. |
| 6,010,447 A | 1/2000 | Kardjian |

(56) References Cited

U.S. PATENT DOCUMENTS

| | | |
|---|---|---|
| 6,030,393 A | 2/2000 | Corlew |
| 6,031,148 A | 2/2000 | Hayes et al. |
| 6,039,686 A | 3/2000 | Kovac |
| 6,042,534 A | 3/2000 | Gellman et al. |
| 6,042,536 A | 3/2000 | Tihon et al. |
| 6,042,583 A | 3/2000 | Thompson et al. |
| 6,048,306 A | 4/2000 | Spielberg |
| 6,048,351 A | 4/2000 | Gordon et al. |
| 6,050,937 A | 4/2000 | Benderev |
| 6,053,935 A | 4/2000 | Brenneman et al. |
| 6,056,688 A | 5/2000 | Benderev et al. |
| 6,063,094 A | 5/2000 | Rosenberg |
| 6,068,591 A | 5/2000 | Bruckner et al. |
| 6,071,290 A | 6/2000 | Compton |
| 6,074,341 A | 6/2000 | Anderson et al. |
| 6,077,216 A | 6/2000 | Benderev et al. |
| 6,090,116 A | 7/2000 | D'Aversa et al. |
| 6,106,545 A | 8/2000 | Egan |
| 6,110,101 A | 8/2000 | Tihon et al. |
| 6,117,067 A | 9/2000 | Gil Vernet |
| 6,159,207 A | 12/2000 | Yoon |
| 6,162,962 A | 12/2000 | Hinsch et al. |
| 6,168,611 B1 | 1/2001 | Rizvi |
| 6,174,329 B1 | 1/2001 | Callol et al. |
| 6,190,401 B1 | 2/2001 | Green et al. |
| 6,197,036 B1 | 3/2001 | Tripp et al. |
| 6,200,330 B1 | 3/2001 | Benderev et al. |
| 6,221,005 B1 | 4/2001 | Bruckner et al. |
| 6,221,060 B1 | 4/2001 | Willard |
| 6,231,496 B1 | 5/2001 | Wilk et al. |
| 6,245,082 B1 | 6/2001 | Gellman et al. |
| 6,264,676 B1 | 7/2001 | Gellman et al. |
| 6,267,772 B1 | 7/2001 | Mulhauser et al. |
| 6,273,852 B1 | 8/2001 | Lehe et al. |
| 6,287,316 B1 | 9/2001 | Agarwal et al. |
| 6,292,700 B1 | 9/2001 | Morrison et al. |
| 6,302,840 B1 | 10/2001 | Benderev |
| 6,306,079 B1 | 10/2001 | Trabucco |
| 6,319,264 B1 | 11/2001 | Tormala et al. |
| 6,328,686 B1 | 12/2001 | Kovac |
| 6,328,744 B1 | 12/2001 | Harari et al. |
| 6,334,446 B1 | 1/2002 | Beyar |
| 6,336,731 B1 | 1/2002 | Chien |
| 6,352,553 B1 | 3/2002 | van der Burg et al. |
| 6,355,065 B1 | 3/2002 | Gabbay |
| 6,382,214 B1 | 5/2002 | Raz et al. |
| 6,387,041 B1 | 5/2002 | Harari et al. |
| 6,406,423 B1 | 6/2002 | Scetbon |
| 6,406,480 B1 | 6/2002 | Beyar et al. |
| 6,408,656 B1 | 6/2002 | Ory et al. |
| 6,418,930 B1 | 7/2002 | Fowler |
| 6,440,154 B2 | 8/2002 | Gellman et al. |
| 6,443,964 B1 | 9/2002 | Ory et al. |
| 6,461,332 B1 | 10/2002 | Mosel et al. |
| 6,475,139 B1 | 11/2002 | Miller |
| 6,478,727 B2 | 11/2002 | Scetbon |
| 6,478,791 B1 | 11/2002 | Carter et al. |
| 6,482,214 B1 | 11/2002 | Sidor, Jr. et al. |
| 6,491,703 B1 | 12/2002 | Ulmsten |
| 6,494,887 B1 | 12/2002 | Kaladelfos |
| 6,494,906 B1 | 12/2002 | Owens |
| 6,502,578 B2 | 1/2003 | Raz et al. |
| 6,506,190 B1 | 1/2003 | Walshe |
| 6,527,802 B1 | 3/2003 | Mayer |
| 6,530,943 B1 | 3/2003 | Hoepffner et al. |
| 6,544,273 B1 | 4/2003 | Harari et al. |
| 6,575,897 B1 | 6/2003 | Ory et al. |
| 6,575,998 B2 | 6/2003 | Beyar |
| 6,582,443 B2 | 6/2003 | Cabak et al. |
| 6,592,515 B2 | 7/2003 | Thierfelder et al. |
| 6,596,001 B2 | 7/2003 | Stormby et al. |
| 6,599,235 B2 | 7/2003 | Kovac |
| 6,599,318 B1 | 7/2003 | Gabbay |
| 6,599,323 B2 | 7/2003 | Melican et al. |
| 6,612,977 B2 | 9/2003 | Staskin et al. |
| 6,638,210 B2 | 10/2003 | Berger |
| 6,638,211 B2 | 10/2003 | Suslian et al. |
| 6,638,284 B1 | 10/2003 | Rousseau et al. |
| 6,641,524 B2 | 11/2003 | Kovac |
| 6,641,525 B2 | 11/2003 | Rocheleau et al. |
| 6,652,450 B2 | 11/2003 | Neisz et al. |
| 6,652,595 B1 | 11/2003 | Nicolo |
| 6,666,817 B2 | 12/2003 | Li |
| 6,669,706 B2 | 12/2003 | Schmitt et al. |
| 6,669,735 B1 | 12/2003 | Pelissier |
| 6,673,010 B2 | 1/2004 | Skiba et al. |
| 6,675,483 B2 | 1/2004 | Bond et al. |
| 6,679,896 B2 | 1/2004 | Gellman et al. |
| 6,689,047 B2 | 2/2004 | Gellman |
| 6,691,711 B2 | 2/2004 | Raz et al. |
| 6,695,855 B1 | 2/2004 | Gaston |
| 6,702,827 B1 | 3/2004 | Lund et al. |
| 6,708,056 B2 | 3/2004 | Duchon et al. |
| 6,737,371 B1 | 5/2004 | Planck et al. |
| 6,755,781 B2 | 6/2004 | Gellman |
| 6,764,474 B2 | 7/2004 | Nielsen et al. |
| 6,783,554 B2 | 8/2004 | Amara et al. |
| 6,786,861 B1 | 9/2004 | Pretorius |
| 6,830,052 B2 | 12/2004 | Carter et al. |
| 6,860,887 B1 | 3/2005 | Frankle |
| 6,878,756 B2 | 4/2005 | Cinelli et al. |
| 6,884,212 B2 | 4/2005 | Thierfelder et al. |
| 6,911,003 B2 | 6/2005 | Anderson et al. |
| 6,932,759 B2 | 8/2005 | Kammerer et al. |
| 6,936,052 B2 | 8/2005 | Gellman et al. |
| 6,953,428 B2 | 10/2005 | Gellman et al. |
| 6,960,160 B2 | 11/2005 | Browning |
| 6,966,918 B1 | 11/2005 | Schuldt-Hempe et al. |
| 7,025,063 B2 | 4/2006 | Snitkin et al. |
| 7,063,716 B2 | 6/2006 | Cunningham |
| 7,070,556 B2 | 7/2006 | Anderson et al. |
| 7,070,558 B2 | 7/2006 | Gellman et al. |
| 7,087,065 B2 | 8/2006 | Ulmsten et al. |
| 7,094,199 B2 | 8/2006 | Petros et al. |
| 7,112,171 B2 | 9/2006 | Rocheleau et al. |
| 7,112,210 B2 | 9/2006 | Ulmsten et al. |
| 7,131,943 B2 | 11/2006 | Kammerer |
| 7,131,944 B2 | 11/2006 | Jacquetin |
| 7,140,956 B1 | 11/2006 | Korovin et al. |
| 7,156,858 B2 | 1/2007 | Schuldt Hempe et al. |
| 7,204,802 B2 | 4/2007 | De Leval |
| 7,229,404 B2 | 6/2007 | Bouffier |
| 7,288,063 B2 | 10/2007 | Petros et al. |
| 7,290,410 B2 | 11/2007 | Meneghin et al. |
| 7,297,102 B2 | 11/2007 | Smith et al. |
| 7,326,213 B2 | 2/2008 | Benderev |
| 7,347,812 B2 | 3/2008 | Mellier |
| 7,371,245 B2 | 5/2008 | Evans et al. |
| 7,387,634 B2 | 6/2008 | Benderev |
| 7,395,822 B1 | 7/2008 | Burton et al. |
| 7,404,819 B1 | 7/2008 | Darios et al. |
| 7,410,460 B2 | 8/2008 | Benderev |
| 7,500,945 B2 | 3/2009 | Cox et al. |
| 7,517,313 B2 | 4/2009 | Thierfelder et al. |
| 7,527,633 B2 | 5/2009 | Rioux |
| 7,559,885 B2 | 7/2009 | Merade et al. |
| 7,594,921 B2 | 9/2009 | Browning |
| 7,601,118 B2 | 10/2009 | Smith et al. |
| 7,611,454 B2 | 11/2009 | De Leval |
| 7,614,258 B2 | 11/2009 | Cherok et al. |
| 7,621,864 B2 | 11/2009 | Suslian et al. |
| 7,628,156 B2 | 12/2009 | Astani et al. |
| 7,673,631 B2 | 3/2010 | Astani et al. |
| 7,686,760 B2 | 3/2010 | Anderson et al. |
| 7,691,050 B2 | 4/2010 | Gellman et al. |
| 7,713,188 B2 | 5/2010 | Bouffier |
| 7,722,528 B2 | 5/2010 | Arnal et al. |
| 7,740,576 B2 | 6/2010 | Hodroff et al. |
| 7,766,926 B2 | 8/2010 | Bosley, Jr. et al. |
| 7,789,821 B2 | 9/2010 | Browning |
| 7,794,385 B2 | 9/2010 | Rosenblatt |
| 7,815,662 B2 | 10/2010 | Spivey et al. |
| 7,927,342 B2 | 4/2011 | Rioux |
| 7,975,698 B2 | 7/2011 | Browning |

(56) References Cited

U.S. PATENT DOCUMENTS

| | | |
|---|---|---|
| 7,981,022 B2 | 7/2011 | Gellman et al. |
| 8,007,430 B2 | 8/2011 | Browning |
| 8,016,741 B2 | 9/2011 | Weiser et al. |
| 8,016,743 B2 | 9/2011 | Maroto |
| 8,047,983 B2 | 11/2011 | Browning |
| 8,092,366 B2 | 1/2012 | Evans |
| 8,097,007 B2 | 1/2012 | Evans et al. |
| 8,100,924 B2 | 1/2012 | Browning |
| 8,118,727 B2 | 2/2012 | Browning |
| 8,118,728 B2 | 2/2012 | Browning |
| 8,123,673 B2 | 2/2012 | Browning |
| 8,128,554 B2 | 3/2012 | Browning |
| 8,157,821 B2 | 4/2012 | Browning |
| 8,157,822 B2 | 4/2012 | Browning |
| 8,162,818 B2 | 4/2012 | Browning |
| 8,167,785 B2 | 5/2012 | Browning |
| 8,182,412 B2 | 5/2012 | Browning |
| 8,182,413 B2 | 5/2012 | Browning |
| 8,182,545 B2 | 5/2012 | Cherok et al. |
| 8,215,310 B2 | 7/2012 | Browning |
| 8,273,011 B2 | 9/2012 | Browning |
| 8,449,450 B2 | 5/2013 | Browning |
| 8,454,492 B2 | 6/2013 | Browning |
| 8,469,875 B2 | 6/2013 | Suslian et al. |
| 8,469,877 B2 | 6/2013 | Browning |
| 8,512,223 B2 | 8/2013 | Browning |
| 8,574,148 B2 | 11/2013 | Browning et al. |
| 8,603,119 B2 | 12/2013 | Browning |
| 8,603,120 B2 | 12/2013 | Browning |
| 8,632,554 B2 | 1/2014 | Browning |
| 8,668,635 B2 | 3/2014 | Browning |
| 8,709,471 B2 | 4/2014 | Browning |
| 8,801,596 B2 | 8/2014 | Browning |
| 8,821,369 B2 | 9/2014 | Browning |
| 8,821,370 B2 | 9/2014 | Browning |
| 8,852,075 B2 | 10/2014 | Browning |
| 9,005,222 B2 | 4/2015 | Evans et al. |
| 2001/0000533 A1 | 4/2001 | Kovac |
| 2001/0018549 A1 | 8/2001 | Scetbon |
| 2001/0039423 A1 | 11/2001 | Skiba et al. |
| 2001/0049467 A1 | 12/2001 | Lehe et al. |
| 2001/0049538 A1 | 12/2001 | Trabucco |
| 2001/0051815 A1 | 12/2001 | Esplin |
| 2001/0053916 A1 | 12/2001 | Rioux |
| 2002/0005204 A1 | 1/2002 | Benderev et al. |
| 2002/0007222 A1 | 1/2002 | Desai |
| 2002/0022841 A1 | 2/2002 | Kovac |
| 2002/0028980 A1 | 3/2002 | Thierfelder et al. |
| 2002/0042658 A1 | 4/2002 | Tyagi |
| 2002/0049503 A1 | 4/2002 | Milbocker |
| 2002/0052612 A1 | 5/2002 | Schmitt et al. |
| 2002/0052653 A1 | 5/2002 | Durgin |
| 2002/0052654 A1 | 5/2002 | Darois et al. |
| 2002/0055748 A1 | 5/2002 | Gellman et al. |
| 2002/0058959 A1 | 5/2002 | Gellman |
| 2002/0058980 A1 | 5/2002 | Sass |
| 2002/0068948 A1 | 6/2002 | Stormby et al. |
| 2002/0072694 A1 | 6/2002 | Snitkin et al. |
| 2002/0077526 A1 | 6/2002 | Kammerer et al. |
| 2002/0078964 A1 | 6/2002 | Kovac et al. |
| 2002/0082619 A1 | 6/2002 | Cabak et al. |
| 2002/0083949 A1 | 7/2002 | James |
| 2002/0091298 A1 | 7/2002 | Landgrebe |
| 2002/0091373 A1 | 7/2002 | Berger |
| 2002/0099258 A1 | 7/2002 | Staskin et al. |
| 2002/0099259 A1 | 7/2002 | Anderson et al. |
| 2002/0099260 A1 | 7/2002 | Suslian et al. |
| 2002/0103542 A1 | 8/2002 | Bilbo |
| 2002/0107430 A1 | 8/2002 | Neisz et al. |
| 2002/0107525 A1 | 8/2002 | Harari et al. |
| 2002/0115906 A1 | 8/2002 | Miller |
| 2002/0119177 A1 | 8/2002 | Bowman et al. |
| 2002/0128670 A1 | 9/2002 | Ulmsten et al. |
| 2002/0138025 A1 | 9/2002 | Gellman et al. |
| 2002/0147382 A1 | 10/2002 | Neisz et al. |
| 2002/0151762 A1 | 10/2002 | Rocheleau et al. |
| 2002/0151909 A1 | 10/2002 | Gellman et al. |
| 2002/0151910 A1 | 10/2002 | Gellman et al. |
| 2002/0156487 A1 | 10/2002 | Gellman et al. |
| 2002/0156488 A1 | 10/2002 | Gellman et al. |
| 2002/0161382 A1 | 10/2002 | Neisz et al. |
| 2002/0183588 A1 | 12/2002 | Fierro |
| 2002/0188169 A1 | 12/2002 | Kammerer et al. |
| 2003/0004395 A1 | 1/2003 | Therin |
| 2003/0009181 A1 | 1/2003 | Gellman et al. |
| 2003/0023136 A1 | 1/2003 | Raz et al. |
| 2003/0023137 A1 | 1/2003 | Gellman |
| 2003/0023138 A1 | 1/2003 | Luscombe |
| 2003/0036676 A1 | 2/2003 | Scetbon |
| 2003/0050530 A1 | 3/2003 | Neisz et al. |
| 2003/0065246 A1 | 4/2003 | Inman et al. |
| 2003/0065402 A1 | 4/2003 | Anderson et al. |
| 2003/0069469 A1 | 4/2003 | Li |
| 2003/0078468 A1 | 4/2003 | Skiba et al. |
| 2003/0100954 A1 | 5/2003 | Schuldt Hempe et al. |
| 2003/0130670 A1 | 7/2003 | Anderson et al. |
| 2003/0149440 A1 | 8/2003 | Kammerer et al. |
| 2003/0171644 A1 | 9/2003 | Anderson et al. |
| 2003/0176762 A1 | 9/2003 | Kammerer |
| 2003/0176875 A1 | 9/2003 | Anderson et al. |
| 2003/0191360 A1 | 10/2003 | Browning |
| 2003/0199732 A1 | 10/2003 | Suslian et al. |
| 2003/0212305 A1 | 11/2003 | Anderson et al. |
| 2003/0220538 A1 | 11/2003 | Jacquetin |
| 2004/0029478 A1 | 2/2004 | Planck et al. |
| 2004/0034373 A1 | 2/2004 | Schuldt Hempe et al. |
| 2004/0039453 A1 | 2/2004 | Anderson et al. |
| 2004/0059356 A1 | 3/2004 | Gingras |
| 2004/0097974 A1 | 5/2004 | De Leval |
| 2004/0106847 A1 | 6/2004 | Benderev |
| 2004/0144395 A1 | 7/2004 | Evans et al. |
| 2004/0172048 A1 | 9/2004 | Browning |
| 2004/0231678 A1 | 11/2004 | Fierro |
| 2004/0243166 A1 | 12/2004 | Odermatt et al. |
| 2004/0249240 A1 | 12/2004 | Goldmann et al. |
| 2004/0249373 A1 | 12/2004 | Gronemeyer et al. |
| 2004/0249397 A1 | 12/2004 | Delorme et al. |
| 2004/0249473 A1 | 12/2004 | Delorme et al. |
| 2005/0000524 A1 | 1/2005 | Cancel et al. |
| 2005/0004576 A1 | 1/2005 | Benderev |
| 2005/0065486 A1 | 3/2005 | Fattman |
| 2005/0080317 A1 | 4/2005 | Merade |
| 2005/0107805 A1 | 5/2005 | Bouffier et al. |
| 2005/0131274 A1 | 6/2005 | Suslian et al. |
| 2005/0240076 A1 | 10/2005 | Neisz et al. |
| 2005/0277806 A1 | 12/2005 | Cristalli |
| 2005/0278037 A1 | 12/2005 | Delorme et al. |
| 2005/0283040 A1 | 12/2005 | Greenhalgh |
| 2006/0015069 A1 | 1/2006 | Evans et al. |
| 2006/0025649 A1 | 2/2006 | Smith et al. |
| 2006/0025783 A1 | 2/2006 | Smith et al. |
| 2006/0041185 A1 | 2/2006 | Browning |
| 2006/0058578 A1 | 3/2006 | Browning |
| 2006/0089524 A1 | 4/2006 | Chu |
| 2006/0089525 A1 | 4/2006 | Mamo et al. |
| 2006/0130848 A1 | 6/2006 | Carey |
| 2006/0205995 A1 | 9/2006 | Browning |
| 2006/0264698 A1 | 11/2006 | Kondonis et al. |
| 2007/0015953 A1 | 1/2007 | MacLean |
| 2007/0020311 A1 | 1/2007 | Browning |
| 2007/0032695 A1 | 2/2007 | Weiser |
| 2007/0032881 A1 | 2/2007 | Browning |
| 2007/0059199 A1 | 3/2007 | Labuschagne |
| 2007/0149555 A1 | 6/2007 | Kase et al. |
| 2007/0219606 A1 | 9/2007 | Moreci et al. |
| 2008/0021263 A1 | 1/2008 | Escude et al. |
| 2008/0161837 A1 | 7/2008 | Toso et al. |
| 2008/0161850 A1 | 7/2008 | Weisenburgh et al. |
| 2008/0167518 A1 | 7/2008 | Burton et al. |
| 2008/0196729 A1 | 8/2008 | Browning |
| 2008/0200751 A1 | 8/2008 | Browning |
| 2008/0281148 A1 | 11/2008 | Evans et al. |
| 2009/0123522 A1 | 5/2009 | Browning |
| 2009/0137862 A1 | 5/2009 | Evans et al. |

(56) References Cited

U.S. PATENT DOCUMENTS

| | | | |
|---|---|---|---|
| 2009/0171377 A1 | 7/2009 | Intoccia et al. |
| 2009/0221868 A1 | 9/2009 | Evans |
| 2009/0287229 A1 | 11/2009 | Ogdahl |
| 2010/0022822 A1 | 1/2010 | Walshe |
| 2010/0056856 A1 | 3/2010 | Suslian et al. |
| 2010/0063351 A1 | 3/2010 | Witzmann et al. |
| 2010/0113869 A1 | 5/2010 | Goldman |
| 2010/0130814 A1 | 5/2010 | Dubernard |
| 2010/0198002 A1 | 8/2010 | O'Donnell |
| 2010/0222794 A1 | 9/2010 | Browning |
| 2010/0222974 A1 | 9/2010 | Nakamura et al. |
| 2010/0256442 A1 | 10/2010 | Ogdahl et al. |
| 2010/0274074 A1 | 10/2010 | Khamis et al. |
| 2010/0280308 A1 | 11/2010 | Browning |
| 2010/0298630 A1 | 11/2010 | Wignall |
| 2011/0021868 A1 | 1/2011 | Browning |
| 2011/0034759 A1 | 2/2011 | Ogdahl et al. |
| 2011/0105833 A1 | 5/2011 | Gozzi et al. |
| 2011/0124954 A1 | 5/2011 | Ogdahl et al. |
| 2011/0124956 A1 | 5/2011 | Mujwid et al. |
| 2011/0201872 A1 | 8/2011 | Browning |
| 2011/0230705 A1 | 9/2011 | Borwning |
| 2011/0230708 A1 | 9/2011 | Browning |
| 2011/0230709 A1 | 9/2011 | Browning |
| 2011/0237865 A1 | 9/2011 | Browning |
| 2011/0237866 A1 | 9/2011 | Browning |
| 2011/0237867 A1 | 9/2011 | Browning |
| 2011/0237868 A1 | 9/2011 | Browning |
| 2011/0237869 A1 | 9/2011 | Browning |
| 2011/0237870 A1 | 9/2011 | Browning |
| 2011/0237873 A1 | 9/2011 | Browning |
| 2011/0237874 A1 | 9/2011 | Browning |
| 2011/0237875 A1 | 9/2011 | Browning |
| 2011/0237876 A1 | 9/2011 | Browning |
| 2011/0237877 A1 | 9/2011 | Browning |
| 2011/0237878 A1 | 9/2011 | Browning |
| 2011/0237879 A1 | 9/2011 | Browning |
| 2011/0238095 A1 | 9/2011 | Browning |
| 2011/0245594 A1 | 10/2011 | Browning |
| 2011/0282136 A1 | 11/2011 | Browning |
| 2011/0319705 A1 | 12/2011 | Browning |
| 2011/0319706 A1 | 12/2011 | Browning |
| 2012/0083649 A1 | 4/2012 | Suslian et al. |
| 2012/0083651 A1 | 4/2012 | Browning |
| 2012/0116154 A1 | 5/2012 | Evans et al. |
| 2012/0143000 A1 | 6/2012 | Browning |
| 2012/0149977 A1 | 6/2012 | Browning |
| 2012/0199133 A1 | 8/2012 | Browning |
| 2013/0281775 A1 | 10/2013 | Browning |
| 2013/0289340 A1 | 10/2013 | Browning |
| 2013/0289341 A1 | 10/2013 | Browning |
| 2014/0039244 A1 | 2/2014 | Browning |
| 2014/0039247 A1 | 2/2014 | Browning |
| 2014/0039248 A1 | 2/2014 | Browning |
| 2014/0051917 A1 | 2/2014 | Browning |
| 2014/0303429 A1 | 10/2014 | Evans et al. |
| 2014/0303430 A1 | 10/2014 | Evans et al. |

FOREIGN PATENT DOCUMENTS

| | | |
|---|---|---|
| DE | 4220283 A1 | 12/1993 |
| DE | 4304353 A1 | 4/1994 |
| DE | 10019604 C2 | 6/2002 |
| DE | 10211360 A1 | 10/2003 |
| EP | 0009072 A1 | 4/1980 |
| EP | 0024781 B1 | 8/1984 |
| EP | 0024780 B1 | 10/1984 |
| EP | 0248544 B1 | 4/1991 |
| EP | 0437481 B1 | 7/1991 |
| EP | 0139286 B1 | 8/1991 |
| EP | 0470308 A1 | 2/1992 |
| EP | 0556313 B1 | 8/1993 |
| EP | 0557964 A1 | 9/1993 |
| EP | 0632999 A1 | 1/1995 |
| EP | 0650703 A1 | 5/1995 |
| EP | 0706778 A1 | 4/1996 |
| EP | 0740925 B1 | 11/1996 |
| EP | 0745351 A2 | 12/1996 |
| EP | 0778749 B1 | 6/1997 |
| EP | 0854691 B1 | 7/1998 |
| EP | 0983033 B1 | 3/2000 |
| EP | 1093758 A1 | 4/2001 |
| EP | 0719527 B1 | 8/2001 |
| EP | 1151722 B1 | 11/2001 |
| EP | 1159921 A2 | 12/2001 |
| EP | 0643945 B1 | 3/2002 |
| EP | 1342454 B1 | 9/2003 |
| EP | 1545285 B1 | 6/2005 |
| EP | 1060714 B1 | 8/2006 |
| EP | 1274370 B1 | 9/2006 |
| EP | 1296614 B1 | 9/2006 |
| EP | 1353598 B1 | 10/2007 |
| EP | 0797962 B2 | 9/2009 |
| FR | 1274370 A | 10/1961 |
| FR | 2712177 A1 | 5/1995 |
| FR | 2732582 A1 | 10/1997 |
| FR | 2735015 A1 | 2/1998 |
| FR | 2811218 E | 11/2000 |
| FR | 2787990 A1 | 4/2001 |
| GB | 0378288 A | 8/1932 |
| GB | 2353220 A | 2/2001 |
| JP | 4452180 B2 | 11/2005 |
| RU | 2187251 C1 | 8/2002 |
| RU | 2196518 C2 | 1/2003 |
| SU | 1225547 A1 | 4/1986 |
| SU | 1342486 A1 | 10/1987 |
| SU | 1475607 A1 | 4/1989 |
| WO | WO1990003766 A1 | 4/1990 |
| WO | WO1991000714 A1 | 1/1991 |
| WO | WO1993017635 A1 | 9/1993 |
| WO | WO1993019678 A2 | 10/1993 |
| WO | WO1995033454 A1 | 12/1995 |
| WO | WO1996003091 A1 | 2/1996 |
| WO | WO1996006567 A1 | 3/1996 |
| WO | WO199706567 A1 | 2/1997 |
| WO | WO1997013465 A1 | 4/1997 |
| WO | WO1997022310 A2 | 6/1997 |
| WO | WO1997043982 A1 | 11/1997 |
| WO | WO1998019606 A1 | 5/1998 |
| WO | WO1998035606 A2 | 8/1998 |
| WO | WO1998035616 A1 | 8/1998 |
| WO | WO1998035632 A1 | 8/1998 |
| WO | WO1998057590 A1 | 12/1998 |
| WO | WO1999016381 A1 | 4/1999 |
| WO | WO1999052450 A1 | 10/1999 |
| WO | WO1999059477 A1 | 11/1999 |
| WO | WO2000007520 A1 | 2/2000 |
| WO | WO2000013601 A1 | 3/2000 |
| WO | WO2000015141 A1 | 3/2000 |
| WO | 2000018325 A1 | 4/2000 |
| WO | WO2000018319 A1 | 4/2000 |
| WO | 2000027304 A1 | 5/2000 |
| WO | WO2000038784 A1 | 7/2000 |
| WO | WO2000057812 A1 | 10/2000 |
| WO | 2000066030 A1 | 11/2000 |
| WO | WO2000064370 A1 | 11/2000 |
| WO | WO2000074594 A1 | 12/2000 |
| WO | WO2000074613 A1 | 12/2000 |
| WO | WO2000074633 A2 | 12/2000 |
| WO | WO2001006951 A1 | 2/2001 |
| WO | WO2001026581 A1 | 4/2001 |
| WO | WO2001039670 A1 | 6/2001 |
| WO | WO2001045589 A1 | 6/2001 |
| WO | 2001052750 A1 | 7/2001 |
| WO | WO2001052729 A2 | 7/2001 |
| WO | WO2001056499 A1 | 8/2001 |
| WO | WO2001080773 A1 | 11/2001 |
| WO | WO2002002031 A1 | 1/2002 |
| WO | 2002019946 A2 | 3/2002 |
| WO | 2002028315 A2 | 4/2002 |
| WO | WO2002026108 A2 | 4/2002 |
| WO | WO2002028312 A1 | 4/2002 |
| WO | WO2002030293 A1 | 4/2002 |
| WO | WO2002032284 A2 | 4/2002 |

(56) References Cited

FOREIGN PATENT DOCUMENTS

| | | |
|---|---|---|
| WO | WO2002032346 A1 | 4/2002 |
| WO | 2002039914 A1 | 5/2002 |
| WO | WO2002034124 A2 | 5/2002 |
| WO | WO2002039890 A2 | 5/2002 |
| WO | 2002058562 A1 | 8/2002 |
| WO | 2002058563 A1 | 8/2002 |
| WO | 2002058564 A2 | 8/2002 |
| WO | 2002058565 A2 | 8/2002 |
| WO | 2002062237 A1 | 8/2002 |
| WO | 2002065922 A1 | 8/2002 |
| WO | 2002065923 A1 | 8/2002 |
| WO | WO2002060371 A1 | 8/2002 |
| WO | WO2002065921 A1 | 8/2002 |
| WO | WO2002065944 A1 | 8/2002 |
| WO | 2002071931 A1 | 9/2002 |
| WO | WO2002069781 A2 | 9/2002 |
| WO | WO2002071953 A2 | 9/2002 |
| WO | WO2002078548 A1 | 10/2002 |
| WO | WO2002078552 A1 | 10/2002 |
| WO | WO2002078568 A1 | 10/2002 |
| WO | WO2002078571 A2 | 10/2002 |
| WO | 2002098322 A1 | 12/2002 |
| WO | WO2002098340 A1 | 12/2002 |
| WO | WO2003002027 A1 | 1/2003 |
| WO | 2003013369 A1 | 2/2003 |
| WO | WO2003013392 A1 | 2/2003 |
| WO | WO2003057074 A2 | 7/2003 |
| WO | WO2003068107 A1 | 8/2003 |
| WO | 2003075792 A1 | 9/2003 |
| WO | WO2003022260 B1 | 10/2003 |
| WO | WO2003086205 A2 | 10/2003 |
| WO | 2003096928 A1 | 11/2003 |
| WO | 2003096930 A1 | 11/2003 |
| WO | WO2003092546 A2 | 11/2003 |
| WO | WO2003094781 A1 | 11/2003 |
| WO | WO2004002370 A1 | 1/2004 |
| WO | WO2004002379 A1 | 1/2004 |
| WO | WO2004004600 A1 | 1/2004 |
| WO | 2004016196 A2 | 2/2004 |
| WO | WO2004012626 A1 | 2/2004 |
| WO | 2004019786 A1 | 3/2004 |
| WO | 2004012579 A2 | 5/2004 |
| WO | WO2004098461 A2 | 11/2004 |
| WO | WO2005018494 A1 | 3/2005 |
| WO | WO2005112842 A1 | 12/2005 |
| WO | WO2006015031 A2 | 2/2006 |
| WO | WO2006015042 A1 | 2/2006 |
| WO | WO2006136625 A1 | 12/2006 |
| WO | WO2007059199 A2 | 5/2007 |
| WO | WO2007149555 A2 | 12/2007 |
| WO | WO2008007086 A2 | 1/2008 |
| WO | WO2008018494 A1 | 2/2008 |

OTHER PUBLICATIONS

Pelosi II and Pelosi III, "New transobturator sling reduces risk of injury," OBG Management, 2003, pp. 17-37.
Pelosi III and Pelosi. Pubic Bone Suburethral Stabilization Sling: Laparoscopic Assessment of a Transvaginal Operation for the Treatment of Stress Urinary Incontinence. Journal of Laparoendoscopic & Advanced Surgical Techniques: 9(1): 45-50, 1999.
Penson and Raz, "Why Anti-incontinence Surgery Succeeds or Fails," Female Urology, 1996, Raz (ed.), W.B. Saunders Company, Chapter 41, pp. 435-442.
Pereyra et al., "Pubourethral Supports in Perspective: Modified Pereyra Procedure for Urinary Incontinence," Obstet Gynecol., 1982, 59:643-648.
Petros and Konsky, "Anchoring the midurethra restores bladderneck anatomy and continence," The Lancet, 1999, 354:997-998.
Petros and Ulmsten, "An analysis of rapid pad testing and the history for the diagnosis of stress incontinence," Acta Obstet. Gynecol. Scand., 1992, 71:529-536.
Petros and Ulmsten, "An Anatomical Basis for Success and Failure of Female Incontinence Surgery," Scand. J. Urol. Nephrol., 1993, (Suppl. 153):55-60.
Petros and Ulmsten, "Bladder Instability in Women: A Premature Activation of the Micturition Reflex," Neurourology and Urodynamics, 1993, 12:235-239.
Petros and Ulmsten, "Cough Transmission Ratio: an Indicator of Suburethral Vaginal Wall Tension Rather than Urethral Closure?" Acta Obstet. Gynecol. Scand., 1990, 69(Suppl. 153):37-38.
Petros and Ulmsten, "Cure of Stress Incontinence by Repair of External Anal Sphincter," Acta. Obstet. Gynecol Scand., 1990, 69(Suppl. 153):75.
Petros and Ulmsten, "Cure of Urge Incontinence by the Combined Intravaginal Sling and Tuck Operation," Acta Obstet. Gynecol. Scand, 1990, 69(Suppl. 153)61-62.
Petros and Ulmsten, "Further Development of the Intravaginal Slingplasty Procedure—IVS III—(with midline "tuck")," Scand. J. Urol. Nephrol., Suppl. 153 An Integral Theory and its Method for the Diagnosis and Management of Female Urinary Incontinence: 69-71, 1993.
Petros and Ulmsten, "Non Stress Non Urge Female Urinary Incontinence—Diagnosis and Cure: A Preliminary Report," Acta Obstet. Gynecol. Scand., 1990, 69(Suppl. 153):69-70.
Petros and Ulmsten, "Part I: Theoretical, Morphological, Radiographical Correlations and Clinical Perspective," Scand. J. Urol. Nephrol., 1993, Suppl. 153:5-28.
Petros and Ulmsten, "Part II:The Biomechanics of Vaginal Tissue and supporting Ligaments with Special Relevance to the Pathogenesis of Female Urinary Incontinence," Scand. J. Urol. Nephrol., 1993, Suppl. 153:29-40.
Petros and Ulmsten, "Part III: Surgical Principles Deriving from the Theory," Scand. J. Urol. Nephrol., 1993, Suppl. 153:41-52.
Petros and Ulmsten, "Part IV: Surgical Applications of the Theory—Development of the Intravaginal Sling Plasty (IVS) Procedure," Scand. J. Urol. Nephrol., 1993, Suppl. 153:53-54.
Petros and Ulmsten, "Pinch Test for Diagnosis of Stress Urinary Incontinence," Acta Obstet. Gynecol. Scand., 1990, 69(Suppl. 153):33-35.
Petros and Ulmsten. An Integral Theory of Female Urinary Incontinence. Acta Obstet. Gynecol. Scand., 1990, 69 (Suppl.153):7-31.
Petros and Ulmsten. Pregnancy Effects on the Intravaginal Sling Operation. Acta Obstet. Gynecol. Scand., 69(Suppl. 153 An Integral Theory of Female Urinary Incontinence) :77-78, 1990.
Petros and Ulmsten. The Combined Intravaginal Sling and Tuck Operation. An Ambulatory Procedure for Cure of Stress and Urge Incontinence. Acta Obstet. Gynecol. Scand., 69(Suppl. 153 An Integral Theory of Female Urinary Incontinence): 53-59, 1990.
Petros and Ulmsten. The Development of the Intravaginal Slingplasty Procedure: IVS II—(with bilateral "tucks"). Scand. J. Urol. Nephrol., Suppl. 153 An Integral Theory and its Method for the Diagnosis and Management of Female Urinary Incontinence: 61-67, 1993.
Petros and Ulmsten. The Free Graft Procedure for Cure of the Tethered Vagina Syndrome. Scand. J. Urol. Nephrol., Suppl. 153: 85-87, 1997.
Petros and Ulmsten. The Further Development of the Intravaginal Slingplasty Procedure: IVS IV—(with "double-breasted" unattached vaginal flap repair and "free" vaginal tapes). Scand. J. Urol. Nephrol., Suppl. 153 An Integral Theory and its Method for the Diagnosis and Management of Female Urinary Incontinence: 73-79, 1993.
Petros and Ulmsten. The Intravaginal Slingplasty Procedure: IVS VI—Further Development of the "Double-Breasted" Vaginal Flap Repair—Attached Flap. Scand. J. Urol. Nephrol., Suppl. 153 An Integral Theory and its Method for the Diagnosis and Management of Female Urinary Incontinence: 81-84, 1993.
Petros and Ulmsten. The Posterior Fornix Syndrome: A Multiple Symptom Complex of Pelvic Pain and Abnormal Urinary Symptoms Deriving from Laxity in the Posterior Fornix of Vagina. Scand. J. Urol. Nephrol., Suppl. 153 An Integral Theory and its Method for the Diagnosis and Management of Female Urinary Incontinence: 89-93, 1993.
Petros and Ulmsten. The Role of a Lax Posterior Vaginal Fornix in the Causation of Stress and Urgency Symptoms: A Preliminary

(56) References Cited

OTHER PUBLICATIONS

Report. Acta Obstet. Gynecol. Scand., 69(Suppl. 153 An Integral Theory of Female Urinary Incontinence): 71-73, 1990.
Petros and Ulmsten. The Tethered Vagina Syndrome, Post Surgical Incontinence and I-Plasty Operation for Cure. Acta Obstet. Gynecol. Scand., 69(Suppl.153 An Integral Theory of Female Urinary Incontinence): 63-67, 1990.
Petros and Ulmsten. The Tuck Procedure: A Simplified Vaginal Repair for Treatment of Female Urinary Incontinence. Acta Obstet. Gynecol. Scand., 69(Suppl.153 An Integral Theory of Female Urinary Incontinence): 41-42, 1990.
Petros and Ulmsten. Urethral Pressure Increase on Effort Originates From Within the Urethra, and Continence From Musculovaginal Closure. Neurourology and Urodynamics, 14:337-350, 1995.
Petros, Peter E., et al. The Autogenic Ligament Procedure: A Technique for Planned Formation of an Artificial Neo-Ligament. Acta Obstet. Gynecol. Scand., 69(Suppl. 153 An Integral Theory of Female Urinary Incontinence):43-51, 1990.
Petros. Development of Generic Models for Ambulatory Vaginal Surgery—A Preliminary Report. Int. Urogynecol. J., 9:19-27, 1998.
Plaintiff Coloplast ,A/S's Opening Claim Construction Brief (Jan. 10, 2011) *Coloplast A/S, v. Generic Medical Devices, Inc.,* Court File No. CV 10-227 BHS.
Plaintiff Coloplast A/S's Answer to Defendant Generic Medical Devices, Inc.'s Counterclaims (Mar. 22, 2010) *Coloplast A/S, v. Generic Medical Devices, Inc.,* Court File No. CV10-227 BHS.
Plaintiff Coloplast A/S's Disclosure of Asserted Claims and Infringement Contentions (Jul. 6, 2010) *Coloplast A/S, v. Generic Medical Devices, Inc.,* Court File No. CV '10-227 BHS.
Plaintiff's Reply to Counterclaim (Mar. 30, 2004) *Mentor Corporation v. American Medical Systems, Inc.* (Civ. No. 04-1000).
Product Monograph for Aris Transobturator Tape for the Treatment of Female Stress Urinary Incontinence, 2004, 40 pages.
Rackley, Raymond R., et al. Tension-free Vaginal Tape and Percutaneous Vaginal Tape Sling Procedures. Techniques in Urology, 7(2):90-100, 2001.
Rackley, Raymond. Synthetic Slings: Five Steps for Successful Placement—Follow These Steps to Insert Transvaginal/ Percutaneous Slings Using Vaginal Approach Alone. Urology Times, 28:46-49, 2000.
Random House Webster's Unabridged Dictionary, 2001.
Raz, Shlomo, et al. The Raz Bladder Neck Suspension: Results in 206 Patients. The Journal of Urology: Urological Neurology and Urodynamics, 148:845-850, 1992.
Raz, Shlomo. Modified Bladder Neck Suspension for Female Stress Incontinence. Urology, 17(1):82-85, 1981.
Response to Non-final Office Action filed in U.S. Appl. No. 90/013,843, filed Jul. 14, 2017, 95 pages.
Richardson, David A., et al. Delayed Reaction to the Dacron Buttress Used in Urethropexy. The Journal of Reproductive Medicine, 29(9):689-692, 1984.
Ridley, John H. Appraisal of the Goebell-Frangenheim-Stoeckel Sling Procedure. American Journal of Obstetrics and Gynecology, 95(5):714-721, 1966.
Salamon, Charbel G., et al., Prospective study of an ultra-lightweight polypropylene Y mesh for robotic sacrocolpopexy, International Urogynecological Journal, Published online Jan. 8, 2013, pp. 1371-1375, vol. 24.
Sand et al., "Prospective randomized trial of polyglactin 910 mesh to prevent recurrence of cystoceles and rectoceles," American Journal of Obstetrics & Gynecology vol. 184, Issue 7, pp. 1357-1364, Jun. 2001.
Schettini, M. et al., "Abdominal sacral colpopexy with prolene mesh," Int Urogynecol J Pelvic Floor Dysfunct (1999) 10 (5): 259-299.
Schumpelick, V. et at., "Minimized polypropylene mesh for preperitoneal net plasty (PNP) of incisional hernias," Chirurg 70:422-430 (1999).
Abdel-fattah, Mohamed et al. Evaluation of transobturator tapes (E-TOT) study: randomised prospective single-blinded study comparing inside-out vs. outside-in transobturator tapes in management of urodynamic stress incontinence: Short term outcomes, European Journal of Obstetrics & Gynecology and Reproductive Biology (2009).
Adjustable Mini-Sling, Just-Swing SVS "Secured Vaginal Sling", Polypropylene, Mar. 2010.
Ajust Adjustable Single-Incision Sling, http://www.bardnordic.com, Mar. 1, 2011.
Ajust(TM) Adjustable Single-Incision Sling, retrieved from www.bardnordic.com/main/product.asp?sectionTypeId=2§ion, accessed Mar. 1, 2011, 1 page.
Aldridge, "Transplantation of Fascia for Relief of Urinary Stress Incontinence," Am. J. Obstet. Gynecol., 1942, 44:398-411.
Amended Answer and Counterclaim (Mar. 30, 2004) *American Medical Systems, Inc. v. Mentor Corporation,* Civ. No. 03-5759.
American Heritage Dictionary, 2nd College Edition (1991).
AMS's Reply to Mentor's Counterclaim (Apr. 5, 2004) *American Medical Systems, Inc. v. Mentor Corporation,* Civ. No. 03-CV-5759.
Answer and Counterclaim (Mar. 15, 2004) *American Medical Systems, Inc. v. Mentor Corporation,* Civ. No. 03-5759.
Answer and Counterclaim of American Medical Systems, Inc. (Mar. 11, 2004) *Mentor Corporation v. American Medical Systems, Inc.,* Civ. Case No. 04-1000 DWF/SRN.
Araki et al., "The Loop-Loosening Procedure for Urination Difficulties After Stamey Suspension of the Vesical Neck," J. Urol., 1990, 144:319-323.
Asmussen and Ulmsten, "Simultaneous Urethro-Cystometry with a New Technique," Scand. J. Urol. Nephrol., 1976, 10:7-11.
Beck and McCormick, "Treatment of Urinary Stress Incontinence with Anterior Colporrhaphy," Obstetrics and Gynecology, 1982, 59(3):271-274.
Benderev, "A Modified Percutaneous Outpatient Bladder Neck Suspension System," J. Urol., 1994, 152:2316-2320.
Benderev, "Anchor Fixation and Other Modifications of Endoscopic Bladder Neck Suspension," Urology, 1992, 40 (5):409-418.
Bergman and Elia, "Three surgical procedures for genuine stress incontinence: Five-year follow-up of a prospective randomized study," Am. J. Obstet. Gynecol., 1995, 173:66-71.
BioArc SP Sling Kit, www.AmericanMedicalSystems.com, 2006.
BioArc(R) SP Sling Kit: 12 Step Procedure, American Medical Systems Inc. Online Brochure 2006, 2 pages.
Blaivas and Jacobs, "Pubovaginal Fascial Sling for the Treatment of Complicated Stress Urinary Incontinence," J. Urol., 1991, 145:1214-1218.
Blaivas and Salinas, "Type III Stress Urinary Incontinence: Importance of Proper Diagnosis and Treatment," American College of Surgeons Surgical Forum, 1984, 70.sup.th Annual Clinical Congress, San Francisco, CA, vol. XXXV, pp. 473-474.
Botros, Cystocele and Rectocele Repair: More Success With Mesh? Jun. 2006.
Bryans, "Marlex gauze hammock sling operation with Cooper's ligament attachment in the management of recurrent urinary stress incontinence," Am. J. Obstet. Gynecol., 1979, 133(3):292-294.
Burch, "Urethrovaginal fixation to Cooper's ligament for correction of stress incontinence, cystocele, and prolapse," Am. J. Obstet. Gynecol., 1961, 81(2):281-290.
Canepa, G. et al., "Horseshoe-shaped Marlex mesh for the treatment of pelvic floor prolapse," European Urology (Jan. 2001) 39 (Supl 2): 23-27.
Priority document for GB Application No. 0025068.8, filed Oct. 12, 2000, 38 pages.
Priority document for GB Application No. 0208359.0, filed Apr. 11, 2002, 50 pages.
Priority document for GB Application No. 0411360.1, filed May 21, 2004, 31 pages.
Chen, Biologic Grafts and Synthetic Meshes in Pelvic Reconstructive Surgery, Jun. 2007.
Choe and Staskin, "Gore-Tex Patch Sling: 7 Years Later," Urology, 1999, 54:641-646.
Chopra et al., "Technique of Rectangular Fascial Sling," Female Urology, 1996, Raz (ed.), W.B. Saunders Company, Chapter 34, pp. 392-394.
Churchill's Medical Dictionary (1989).

(56) References Cited

OTHER PUBLICATIONS

Cobb, William S., et al., The Argument for Lightweight Polypropylene Mesh in Hernia Repair, Surgical Innovation, Mar. 2005, vol. 12, No. 1, pp. 63-69.
Complaint and Jury Demand (Feb. 8, 2010), *Coloplast A/S v. Mpathy Medical Devices, Inc.*, Court File No. CV10-206.
Complaint for Declaratory Judgment (Oct. 28, 2003) *American Medical Systems, Inc. v. Mentor Corporation*.
Complaint for Patent Infringement (Feb. 20, 2004) *Mentor Corporation v. American Medical Systems, Inc.*
Complaint for Patent Infringement and Exhibits (Feb. 8, 2010) *Coloplast A/S, v. Generic Medical Devices, Inc.*, Court File No. CV10-227 BHS.
Cook, Urogynecology, Product Technical Datasheet and Order form, 1996.
Cosson et al., "Mechanical properties of synthetic implants used in the repair of prolapse and urinary incontinence in women: which is the ideal material?," Int Urogynecol J (2003) 14: 169-178, Jul. 25, 2003.
Culligan, Patrick J., Clinical Expert Series, "Nonsurgical Management of Pelvic Organ Prolapse", American College of Obstetricians and Gynecologists, vol. 119, No. 4, Apr. 2012, 9 pages.
Culligan, Patrick J., et al., Subjective and objective results 1 year after robotic sacrocolpopexy using a lightweight Y-mesh, International Urogynecological Journal, Published online Nov. 22, 2013, pp. 731-735, vol. 25.
D. Elliott Declaration and Attachment 1 (Jan. 5, 2011) *Coloplast A/S, v. Generic Medical Devices, Inc.*, Court File No. CV 10-227 BHS.
Dargent, D. et al., Pose d'un ruban sous uretral oblique par voie obturatrice dans le traitement de L'incontinence urinary feminine [English "Insertion of a transobturator oblique suburethral sling in the treatment of female urinary incontinence"], Gynecol. Obstet. Ferril. 14, pp. 576-582 (2002) [including English translation at the beginning of document].
Das and Palmer, "Laparoscopic Colpo-Suspension," J. Urol., 1995, 154:1119-1121.
De Leval, J., "Novel Surgical Technique for the Treatment of Female Stress Urinary Continence: Transobturator Vaginal Tape Inside-Out," European Urology, 2003, 44:724-730.
DeBord, James R., (1998), "The Historical Development of Prosthetics in Hernia Surgery," Surgical Clinics of North America, 78(6): 973-1006.
Declaration of Dr. George D. Webster in Support of Generic Medical Devices, Inc.'s Briefing on Claim Construction and Exhibits for *Coloplast A/S, v. Generic Medical Devices, Inc.*, Court File No. CV 10-227 BHS, signed Jan. 5, 2011.
Declaration of Jeya Paul and Attachment 1 (Jan. 10, 2011) *Coloplast A/S, v. Generic Medical Devices, Inc.*, Court File No. CV 10-227 BHS.
Declaration of Marc Belloli in Support of GMD's Opening Claim Construction Brief and Exhibits A-J (Jan. 10, 2011) *Coloplast A/S v. Generic Medical Devices, Inc.*, Court File No. CV 10-227 BHS.
Decter, "Use of the Fascial Sling for Neurogenic Incontinence: Lessons Learned," J. Urol., 1993, 150:683-686.
Delmore, E. et al., La bandelette trans-obturatrice: Un procede mini-invasif pour traiter l'incontinence urinaire d'effort de la femme, Progres en Urologie, vol. 11, pp. 1306-1313 (2001) [including English translation at the beginning of document].
DeTayrac, et al. Prolapse repair by vaginal route using . . . Int. Urogynecol. J. (published online May 13, 2006).
Dwyer, Transvaginal repair of anterior and posterior compartment prolapse with Atrium polypropylene mesh, BJOG: An International Journal of Obstetrics & Gynaecology, Aug. 2004.
Enzelsberger et al., "Urodynamic and Radiologic Parameters Before and After Loop Surgery for Recurrent Urinary Stress Incontinence," Acta Obstet. Gynecol. Scand., 1990, 69:51-54.
Eriksen et al., "Long-Term Effectiveness of the Burch Colposuspension in Female Urinary Stress Incontinence," Acta Obstet. Gynecol. Scand., 1990, 69:45-50.
Exhibit—Caldera Brochure: Caldera Medical, "Vertessa® Lite, Polypropylene Mesh for Sacrocolpopexy," (last accessed Jul. 11, 2017 at http://www.calderamedical.com/wp-content/uploads/VL-Brochure.pdf).
Exhibit—Caldera Press Release: Caldera Medical, "Caldera Medical Announces FDA Clearance of Vertessa™ Lite Polypropylene Mesh for Sacrocopopexy," Jun. 25, 2013 (last accessed Jul. 11, 2017 at http://www.calderamedical.com/wp-content/uploads/Vertessa-Lite_PR-FINAL.pdf).
Exhibit—Smartmesh Materials 1: Mpathy Medical, Smartmesh Technology, product details page, printed from website http://www.mpathymedical.com/foundations/store/sotrepage.asp?page=smartmesh on Apr. 6, 2010, 1pg.
Exhibit—Smartmesh Materials 2: Mpathy Medical, Mpowering Solutions Redefining Surgical Expectations, company and product brochure, 5 pgs.
Exhibit—Smartmesh Materials 3: Mpathy Medical, Physician Testimonials, printed from website http://www.mpathymedical.com/foundations/store/storepage.asp?page=Testimonia on Apr. 6, 2010, 2 pgs.
Exhibit—Smartmesh Materials 4: Mpathy Medical, Restorelle Y, with Smartmesh Technology, product brochure, 1pg.
Falconer et al., "Clinical Outcome and Changes in Connective Tissue Metabolism After Intravaginal Slingplasty in Stress Incontinent Women," Int. Urogynecol. J., 1996, 7:133-137.
Falconer et al., "Influence of Different Sling Materials on Connective Tissue Metabolism in Stress Urinary Incontinent Women," Int. Urogynecol. J., 2001, (Suppl. 2):S19-S23.
Feola, Andrew et al., Characterizing the ex vivo textile and structural properties of synthetic prolapse mesh products, International Urogynecological Journal, Published online Aug. 11, 2012, pp. 559-564, vol. 24.
Feola, Andrew et al., Deterioration in Biomechanical Properties of the Vagina Following Implantation of a High Stiffness Prolapse Mesh, BJOG (International Journal of Obstetrics and Gynaecology) Jan. 2013, pp. 224-232, vol. 120, No. 2.
Generic Medical Devices, Inc 's Answer to Complaint and Counterclaims (Mar. 1, 2010) *Coloplast A/S, v. Generic Medical Devices, Inc.*, Court File No. CV10-227 BHS.
Generic Medical Devices, Inc.'s Non, Infringement and Invalidity Contentions and Accompanying Document Production (Aug. 9, 2010) *Coloplast A/S, v. Generic Medical Devices, Inc.*, Court File No. CV-10-227 BHS.
Generic Medical Devices, Inc.'s Opening Claim Construction Brief (Jan. 10, 2011) *Coloplast A/S, v. Generic Medical Devices, Inc.*, Court File No. CV10-227 BHS.
Gilja et al., "A Modified Raz Bladder Neck Suspension Operation (Transvaginal Burch)," J. Urol., 1995, 153:1455-1457.
Gittes and Loughlin, "No-Incision Pubovaginal Suspension for Stress Incontinence," J. Urol., 1987, 138:568-570.
Greca et al., "The influence of porosity on the integration histology of two polypropylene meshes for the treatment of abdominal wall defects in dogs," Sep. 7, 2007, Hernia (2008) 12:45-49.
Gruss, "The Obturator Bypass. Indications. Techniques. Outcomes," Chirurgie, 1971, 97:220-226.
Guida and Moore, "The Surgeon At Work. Obturator Bypass Technique," Surgery, Gynecology & Obstetrics, 1969, pp. 1307-1315.
Handa et al., "Banked Human Fascia Lata for the Suburethral Sling Procedure: A Preliminary Report," Obstet. Gynecol., 1996, 88:1045-1049.
Hardiman, et al. Cystocele repair using polypropylene mesh. Br. J. Obstet. Gynaecol. 107: 825-26 (2000).
Henriksson and Ulmsten, "A urodynamic evaluation of the effects of abdominal urethrocystopexy and vaginal sling urethroplasty in women with stress incontinence," Am. J. Obstet. Gynecol., 1978, 131:77-82.
Hodgkinson and Kelly, "Urinary Stress Incontinence in the Female. III. Round-ligament technique for retropubic suspension of the urethra," Obstet. Gynecol., 1957, 10:493-499.
Hohenfellner and Petri, "Sling Procedures," Surgery of Female Incontinence, 2nd edition, SpringerVeriag, pp. 105-113, 1986.

(56) References Cited

OTHER PUBLICATIONS

Holschneider et al., "The Modified Pereyra Procedure in Recurrent Stress Urinary Incontinence: A 15-Year Review," Obstet. Gynecol., 1994, 83:573-578.
Horbach et al., "A Suburethral Sling Procedure with Polytetrafluoroethylene for the Treatment of Genuine Stress Incontinence in Patients with Low Urethral Closure Pressure," Obstet. Gynecol., 1988, 71:648-652.
Horbach, "Suburethral Sling Procedures," Urogynecology and Urodynamics—Theory and Practice, 1996, Williams & Wilkins, pp. 569-579.
Iglesia, C.B. et al., The Use of Mesh in Gynecologic Surgery, International Urogynecology Journal, 8 (1997), pp. 105-115, Springer-Verlag London Ltd.
Ingelman-Sundberg and Ulmsten, "Surgical Treatment of Female Urinary Stress Incontinence," Contr. Gynec. Obstet., 1983, 10:51-69.
International Preliminary Examination Report issued in PCT/GB01/04554, completed Nov. 22, 2002, 6 pages.
International Preliminary Examination Report issued in PCT/GB2002/001234, completed Jul. 1, 2003, 18 pages.
International Search Report and Written Opinion issued in PCT/GB2004/001390, dated Sep. 3, 2004, 12 pages.
International Search Report and Written Opinion issued in PCT/US03/24212, dated May 28, 2004, 11 pages.
International Search Report for PCT/GB2009/050174, dated Jun. 24, 2009.
International Search Report issued in PCT/GB01/04554, dated Jan. 29, 2002, 3 pages.
International Search Report issued in PCT/GB2002/01234 dated Jun. 5, 2002, 3 pages.
International Search Report issued in PCT/GB2007/002589, dated Jan. 22, 2008, 5 pages.
Jacquetin, Bernard, "2. Utilisation du "TVT" dans la chirurgie de l'incontinence urinaire feminine", J. Gynecol. Obstet. Biol. Reprod. 29: 242-47 (2000).
Jeffcoate, "The Results of the Aldridge Sling Operation for Stress Incontinence," The Journal of Obstetrics and Gynaecology of the British Empire, 1956, 63:36-39.
Jeter, "The Social Impact of Urinary Incontinence," Female Urology, Raz (ed.), W. B. Saunders Company, 1996, Chapter 7, pp. 80-86.
Joint Claim Construction and Prehearing Statement Pursuant to Local Patent Rule 132 and Appendix A (Nov. 15, 2010) *Coloplast A/S*, v. *Generic Medical Devices, Inc.*, Court File No. CV10-227 BHS.
Just-Swing(R) Adjustable mine-sling, Textile Hi-Tec Online Brochure 2010, 4 pages.
Karram and Bhatia, "Patch Procedure: Modified Transvaginal Fascia Lata Sling for Recurrent or Severe Stress Urinary Incontinence," Obstet Gynecol., 1990, 75:461-463.
Kennelly et al. "Prospective Evaluation of a Single Incision Sling for Stress Urinary Incontinence" The Journal of Urology [Online] 2010, 184, pp. 604-609.
Kerdiles et al., "Bypass via the Obturator Foramen in Reconstructive Arterial Surgery of the Lower Extremities," Ann. Chir. Thorac. Cardio-Vasc., 1974, 13(4)335-341.
Kerr and Staskin, "The Use of Artificial Material for Sling Surgery in the Treatment of Female Stress Urinary Incontinence," Female Urology, 1996, Raz (ed.), W.B. Saunders Company, Chapter 33, pp. 382-391.
Kersey, "The gauze hammock sling operation in the treatment of stress incontinence," Br. J. Obstet. Gynecol., 1983, 90:945-949.
Shaw, W., "An Operation for the Treatment of Stress Incontinence," Br. Med. J. 1949:1070-1073.
Sheiner et al., "An unusual complication of obturator foramen arterial bypass," J. Cardiovasc. Surg., 1969, 10 (4):324-328.
Sirls and Leach, "Use of Fascia Lata for Pubovaginal Sling," Female Urology, 1996, Raz (ed.). W.B. Saunders Company, Chapter 32, pp. 376-381.

Sloan and Barwin, "Stress Incontinence of Urine: A Retrospective Study of the Complications and Late Results of Simple Suprapubic Suburethral Fascial Slings," J. Urol., 1973, 110:533-536.
Solyx™ SIS System, The Carrier Tip That Allows for Advanced Control, (Accessed: Feb. 28, 2011).
Sottner et al. "New Single-Incision Sling System MiniArc™ in treatment of the female stress urinary incontinence" Gynekologicko-porodnická klinika [Online] 2010, 75(2), pp. 101-104.
Spencer et al., "A Comparison of Endoscopic Suspension of the Vesical Neck with Suprapubic Vesicourethropexy for Treatment of Stress Urinary Incontinence," J. Urol., 1987, 137:411-415.
Spinosa, JP et al., Transobturator surgery for female stress incontinence: a comparative anatomical study of outside-in vs. inside-out techniques, BJU Intl., 100(5), pp. 1097-1102 (Nov. 2007).
Stamey, "Endoscopic Suspension of the Vesical Neck for Urinary Incontinence in Females," Annals of Surgery, 1980, 192(4):465-471.
Stanton, Stuart L. Suprapubic Approaches for Stress Incontinence in Women. The Journal of the American Geriatrics Society, 38(3):348-351, 1990.
Staskin et al., "The Gore-tex sling procedure for female sphincteric incontinence: indications, technique, and results," World J. Urol., 1997, 15:295-299.
Stothers et al., "Anterior Vaginal Wall Sling," Female Urology, 1996, Raz (ed.), W.B. Saunders Company, Chapter 35, pp. 395-398.
Supplemental European Search Report issued in EP Application No. 03751825, dated Jun. 19, 2009, 5 pages.
Surgimesh Sling Treatment of Incontinence http://www.aspide.com Mar. 4, 2011.
Ulmsten and Petros, "Intravaginal Slingplasty (IVS): An Ambulatory Surgical Procedure for Treatment of Female Urinary Incontinence," Scand. J. Urol. Nephrol., 1995, 29:75-82.
Ulmsten et al., "A three-year follow up of tension free vaginal tape for surgical treatment of female stress urinary incontinence," Br. J. Obstet. Gynecol., 1999, 106:345-350.
Ulmsten et al., "An Ambulatory Surgical Procedure Under Local Anesthesia for Treatment of Female Urinary Incontinence," Int. Urogynecol. J., 1996, 7:81-86.
Ulmsten et al., "Different Biochemical Composition of Connective Tissue in Continent and Stress Incontinent Women," Acta Obstet. Gynecol. Scand., 1987, 66:455-457.
Ulmsten et al., "The unstable female urethra," Am. J. Obstet. Gynecol., 1982, 144:93-97.
Ulmsten, "Female Urinary Incontinence—A Symptom, Not a Urodynamic Disease. Some Theoretical and Practical Aspects on the Diagnosis and Treatment of Female Urinary Incontinence," Int. Urogynecol. J., 1995, 6:2-3.
Ulstem et al., "A Multicenter Study of Tension-Free Vaginal Tape (TVT) for Surgical Treatment of Stress Urinary Incontinence," Int. Urogynecol. J., 1998, 9:210-213.
U.S. Appl. No. 13/149,994, filed Jun. 1, 2011.
U.S. Appl. No. 60/327,160, filed Oct. 4, 2001.
U.S. Appl. No. 10/106,086, filed Mar. 25, 2002.
U.S. Appl. No. 11/199,061, filed Aug. 8, 2005.
U.S. Appl. No. 60/279,794, filed Mar. 29, 2001.
U.S. Appl. No. 60/302,929, filed Jul. 3, 2001.
U.S. Appl. No. 60/307,836, filed Jul. 25, 2001.
U.S. Appl. No. 60/322,309, filed Sep. 14, 2001.
U.S. Appl. No. 60/362,806, filed Mar. 7, 2002.
U.S. Appl. No. 60/380,797, filed May 14, 2002.
U.S. Appl. No. 60/393,969, filed Jul. 5, 2002.
U.S. Appl. No. 60/402,007, filed Aug. 8, 2002.
U.S. Appl. No. 60/414,865, filed Sep. 30, 2002.
Webster and Kreder, "Voiding Dysfunction Following Cystourethropexy: Its Evaluation and Management," J. Urol., 1990, 144:670-673.
Weidemann, Small Intestinal Submucosa for Pubourethral Sling Suspension for the Treatment of Stress Incontinence: First Histopathological Results in Humans, Jul. 2004.
Winter, "Peripubic Urethropexy for Urinary Stress Incontinence in Women," Urology, 1982, 20(4):408-411.
Woodside and Borden, "Suprapubic Endoscopic Vesical Neck Suspension for the Management of Urinary Incontinence in Myelodysplastic Girls," J. Urol., 1986, 135:97-99.

(56) References Cited

OTHER PUBLICATIONS

Written Opinion for PCT/GB2009/050174, dated Jun. 24, 2009.
Written Opionion issued in PCT/GB2007/002589, dated Jan. 22, 2008, 5 pages.
Zacharin and Hamilton, "Pulsion Enterocele: Long-Term Results of an Abdominoperineal Technique," Obstet. Gynecol., 1980, 55(2):141-148.
Zacharin, "The suspensory mechanism of the female urethra," J. Anat., 1963, 97(3):423-427.
Klinge et al., "Do Multifilament Alloplastic Meshes Increase the Infection Rate? Analysis of the Polymeric Surface, the Bacteria Adherence, and the In Vivo Consequences in a Rat Model," Oct. 17, 2002, Wiley Periodicals, Inc., J Biomed Mater Res (Appl Biomater) 63: 765-771, 2002.
Klinge et al., "Functional and Morphological Evaluation of a Low-Weight, Monofilament Polypropylene Mesh for Hernia Repair," Journal of Biomedical Material Research, Jan. 24, 2002, pp. 129-137.
Klinge, U. et al., "Influence of polyglactin-coating on functional and morphological parameters of polypropylene-mesh modifications for abnormal wall repair," Biomaterials 20 (1999), pp. 613-623.
Klinge, U. et al., "Modified Mesh for Hernia Repair that is Adapted to the Physiology of the Abdominal Wall," Eur J Surg 164:951-960 (1998).
Klinge, U. et al., "Pathophysiology of the abdominal wall," Der Chirurg, (1996),67: 229-233.
Klosterhalfen, B, et al., "Functional and morphological evaluation of different polypropylene-mesh modifications for abdominal wall repair," Biomaterials 19:2235-2246 (1998).
Klosterhalfen, B. et al., "Morphological correlation of the functional mechanics of the abdominal wall after mesh implantation," Langenbecks Arch Chir 382:87-94 (1997).
Klutke et al., "The Anatomy of Stress Incontinence: Magnetic Resonance Imaging of the Female Bladder Neck and Urethra," J. Urol., 1990, 143:563-566.
Klutke et al., "Transvaginal Bladder Neck Suspension to Cooper's Ligament: A Modified Pereyra Procedure," Obstet. Gynecol., 1996, 88:294-297.
Korda et al., "Experience with Silastic Slings for Female Urinary Incontinence," Aust. NZ J. Obstet. Gynaecol., 1989, N:150-154.
Kovac and Cruikshank. Pubic bone suburethral stabilization sling: a long-term cure for SUI? Contemporary OB/GYN: Surgical Techniques, 43(2):52-76, 1998.
Kovac, R. S. Follow-Up of the Pubic Bone Suburethral Stabilization Sling for Recurrent Urinary Incontinence (Kovac Procedure). Journal of Pelvic Surgery, 5(3): 156-160, 1999.
Kovac, R., et. al. Pubic Bone Suburethral Stablization Sling for Recurrent Urinary Incontinence. Obstetrics & Genecology: Instruments & Methods, 89(4): 624-627, Apr. 1997.
Lazarevski, M.B., Suburethral Duplication of the Vaginal Wall—An Original Operation for Urinary Stress Incontinence in Women, 6 Int'l Urogynecol. J. 73-79 (1995).
Leach et al., "Female Stress Urinary Incontinence Clinical Guidelines Panel Summary Report on Surgical Management of Female Stress Urinary Incontinence," J. Urol., 1997, 158:875-880.
Leach, "Bone Fixation Technique for Transvaginal Needle Suspension," Urology, 1988, 31(5):388-390.
Liang, R. et al., Vaginal degeneration following implantation of synthetic mesh with increased stiffness, BJOG (International Journal of Obstetrics and Gynaecology) 2012, pp. 233-243, vol. 120.
Lichtenstein et al., "The Tension-Free Hernioplasty," Am. J. Surgery, 1989, 157:188-193.
Lipton, S. and Estrin, J., "A Biomechanical Study of the Aponeurotic Iguinal Hernia Repair," Journal of the American College of Surgeons, Jun. 1994, vol. 178, pp. 595-599.
Loughlin et al., "Review of an 8-Year Experience with Modifications of Endoscopic Suspension of the Bladder Neck for Female Stress Urinary Incontinence," J. Urol., 1990, 143:44-45.
Maher, Surgical Management of Anterior Vaginal Wall Prolapse: An Evidence Based Literature Review, 2006.

Mahoney and Whelan, "Use of Obturator Foramen in Iliofemoral Artery Grafting: Case Reports," Annals of Surgery, 1966, 163(2):215-220.
Marshall et al., "The Correction of Stress Incontinence by Simple Vesicourethral Suspension," J. Urol., 2002, 168:1326-1331.
McGuire and Gormley, "Abdominal Fascial Slings," Female Urology, 1996, Raz (ed.), W.B. Saunders Company, Chapter 31, pp. 369-375.
McGuire and Lytton, "Pubovaginal Sling Procedure for Stress Incontinence," J. Urol., 1978, 119:82-84.
McGuire et al., "Experience with Pubovaginal Slings for Urinary Incontinence at The University of Michigan," J. Urol., 1987, 138:525-526.
McGuire, "Abdominal Procedures for Stress Incontinence," Urologic Clinics of North America, 1985, 12(2):285-290.
McIndoe et al., "The Aldridge Sling Procedure in the Treatment of Urinary Stress Incontinence," Aust. NZ J. Obstet. Gynaecol., 1987, 27:238-239.
McKiel, Jr. et al., "Marshall-Marchetti Procedure: Modification," J. Urol., 1966, 96:737-739.
Migliari, R. et al., "Tension-Free Vaginal Mesh Repair for Anterior Vaginal Wall Prolapse," European Urology (2000) 38(2): 151-155.
Miklos, Mini Sling Incontinence Treatment—Vagina Plastic Surgery, http://www.miklosandmoore.com/mini_sling.php, Feb. 28, 2011.
MiniArc Single-Incision Sling http://www.americanmedicalsystems.com Mar. 4, 2011.
Moir, "The Gauze-Hammock Operation," The Journal of Obstetrics and Gynaecology of the British Commonwealth, 1968, 75(1):1-9.
Monseur, J., Anatomie Chirurgicale: Les Ligaments Du Perinee Feminin, Sep. 4, 2008.
Moore et al. "Single-Center Retrospective Study of the Technique, Safety, and 12 Month Efficacy or the MiniArc™ Single Incision Sling: A New Minimally Invasive Procedure for Treatment of Female SUI" [Online] 2009, 18, pp. 175-181.
Morgan et al., "The Marlex sling operation for the treatment of recurrent stress urinary incontinence: A 16-year review," Am. J. Obstet. Gynecol., 1985, 151:224-226.
Morgan, "A sling operation, using Marlex polypropylene mesh, for treatment of recurrent stress incontinence," Am. J. Obstet. Gynecol., 1970, 106(3):369-376.
Narik and Palmrich, "A simplified sling operation suitable for routine use," Am. J. Obstet. Gynecol., 1962, 84:400-405.
Nichols, "The Mersilene Mesh Gauze-Hammock for Severe Urinary Stress Incontinence," Obstet. Gynecol., 1973, 41(1):88-93.
Nicita, Giulio, (1998), "A New Operation for Genitourinary Prolapse," The Journal of Urology, 160:741-745.
Nickel et al., "Evaluation of a Transpelvic Sling Procedure With and Without Colpolsuspension for Treatment of Female Dogs With Refractory Urethral Sphincter Mechanism Incompetence," Veterinary Surgery, 1998, 27:94-104.
Non-final Office Action issued in U.S. Appl. No. 90/013,843, dated May 17, 2017, 17 pages.
Norris et al., "Use of Synthetic Material in Sling Surgery: A Minimally Invasive Approach," J. Endocrinology, 1996, 10 (3):227-230.
Novak, "Abdonomovaginal Techniques," Gynecological Surgical Technique, 1977, Piccin Editore, Padua, 5 pages.
O'Donnell, "Combined Raz Urethral Suspension and McGuire Pubovaginal Sling for Treatment of Complicated Stress Urinary Incontinence," J. Arkansas Medical Society, 1992, 88(8):389.
Order dismissing cases (Sep. 16, 2004) Civ. No. 03-5759 and Civ. No. 04-1000.
Ostergard, Donald R., Polypropylene Vaginal Mesh Grafts in Gynecology, American College of Obstetricians and Gynecologists, Oct. 2010, pp. 962-966, vol. 116, No. 4, Published by Lippincott Williams & Wilkins.
P.K. Amid, "Classification of biomaterials and their related complications in abdominal wall hernia surgery," Mar. 25, 1997, Hernia (1997) 1: 15-21.
Pandit et al., "Design of surgical meshes—an engineering perspective," Technology and Health Care 12 (2004) 51-65, Jan. 8, 2004.
Parker, MC and Phillips, RK, "Repair of rectocoele using Marlex mesh," Ann R Coll Surg Engl (May 1993) 75(3): 193-194.

SECTION A-A

SURGICAL IMPLANT CONSISTING OF NON-ABSORBABLE MATERIAL

CROSS-REFERENCE TO RELATED APPLICATIONS

This application is a continuation of U.S. patent application Ser. No. 14/972,133, filed on Dec. 17, 2015, which is a continuation of U.S. patent application Ser. No. 13/316,507, filed on Dec. 11, 2011, which is a continuation of U.S. patent application Ser. No. 12/551,676 filed on Sep. 1, 2009 that has issued as U.S. Pat. No. 8,100,924, which is a continuation of U.S. patent application Ser. No. 10/473,825 filed on Apr. 26, 2004 in the U.S. that has issued as U.S. Pat. No. 7,594,921, and which is the U.S. national phase of International Patent Application No. PCT/GB02/01234, filed Apr. 2, 2002, which claims priority to and the benefit of Great Britain patent Application No. 0108088.6, filed Mar. 30, 2001, the contents of each application being incorporated by reference herein.

The present invention relates to the treatment of a hernia such as a uterovaginal prolapse and, in particular, to a surgical implant for use in such treatment and to a related surgical procedure and device.

A hernia is basically a defect resulting in the protrusion of part of an organ through the wall of a bodily cavity within which it is normally contained. For example, a fairly common and well known type of hernia is a defect in the lower abdominal wall resulting in a sac which may contain a portion of the intestine protruding through the abdominal wall. This is referred to as an inguinal hernia. Similarly, a defect in the abdominal wall after surgery is referred to as an incisional hernia. Another type of hernia is a defect in the pelvic floor or other supporting structures resulting in a portion of the uterus, bladder, bowel or other surrounding tissue protruding through, e.g., the vaginal wall. This is usually referred to as uterovaginal prolapse.

A common way of treating hernias is to repair the defect by sutures, whether or not the hernial sac is also sutured or repaired, in order that the protruding organ is contained in its normal position. As the defect generally comprises a weakening and attenuation leading to parting of tissues in a fascial wall, it is usually necessary to apply tension to the sutures in order to close the parted tissues. Thus, the fascial wall is generally pinched or tensioned around the area of the defect in order to close the parted tissues.

This treatment is generally effective, but does have some inherent problems. In particular, the pinching or tensioning of tissue around the defect can lead to discomfort and/or recurrence of the hernia. Additionally, in the case of uterovaginal prolapse, such pinching or tensioning of the vaginal wall almost inevitably results in anatomical distortion (such as narrowing of the vaginal cavity) with consequential pain and quality of life implications for the patient and relatively high recurrence and/or complication rates.

In order to address these problems, in the case of inguinal hernia repair, it has been suggested to make use of a surgical implant to overlay or close the weakened and parted tissues without the need to pinch or tension the surrounding tissue of the fascia. Such surgical implants generally comprise meshes and are now widely used in inguinal hernia repair. Meshes may be applied subcutaneously (i.e. under the skin), internally or externally of the abdominal wall and may be either absorbable or non-absorbable depending on the nature and severity of the particular defect being treated. Meshes may be applied in combination with sutures to hold the mesh in place or, alternatively, with sutures that close the parted tissues as in a "non-mesh" technique. Meshes are usually applied in open surgical procedures, although they may sometimes be applied in laparoscopic surgical procedures.

A typical mesh for an inguinal hernia repair comprises woven or knitted polypropylene such as Marlex® or Prolene®. Such meshes have a number of desirable properties that make them effective for use in hernia repair. For example, they are made of materials that are suitably inert so as to be less likely to cause adverse reactions when implanted in the body. Furthermore, they are mechanically strong, cheap, easily sterilisable and easy to work with.

However, conventional meshes have a number of inherent problems. For example, fistula or sinus (i.e. abnormal passages between internal organs or between an internal organ and the body surface) can develop as a result of a mesh being implanted and left inside the body. More generally, the placement of a foreign body subcutaneously can also lead to inflammation or infection. Similarly, edge extrusion (i.e. the erosion of body tissue around the edge of the mesh) can occur. Nevertheless, overall, the use of meshes is generally considered to be beneficial in the treatment of incisional and inguinal hernias.

It has also been suggested to use meshes in the treatment of uterovaginal prolapse. Meshes that have been proposed for use in the repair of uterovaginal prolapse are similar to those that are used for the repair of inguinal hernia and such like. However, there is concern that the above mentioned problems with the use of meshes are greater when a mesh is placed in the vaginal wall as this tissue is generally thin only just below the surface and therefore more prone to adverse reactions. Furthermore, the placement of a foreign body close to the rectum and urinary tract may increase the risk of infection, inflammation, erosion, fistula or translocation. Thus, it is a relatively widespread view that the use of meshes in the treatment of vaginal prolapse is less desirable than in the treatment of other hernias.

Nevertheless, as the use of meshes to treat uterovaginal prolapse can avoid anatomical distortion and the above mentioned problems related to this, the Applicant considers there are significant benefits in the use of meshes in the treatment of uterovaginal prolapse should it be possible to mitigate the problems associated with mesh treatment.

The applicant has recognised that there are a number of specific features of conventional meshes that exacerbate the problems of fistula, sinus, edge extrusion, infection etc., particularly when these meshes are implanted in the vaginal wall. The Applicant has therefore realised that it is possible to provide a surgical implant that has the benefits of mesh treatment, i.e. the avoidance of anatomical distortion and its related problems, and also minimises the above mentioned problems.

One specific problem with conventional meshes that the Applicant has recognised is that they have jagged or rough edges. The rough edges arise as conventional meshes are generally formed from sheets of multiple woven or intersecting fibres or strands. When the meshes are cut to size in manufacture or prior to fitting, the stray ends of the fibres or strands are left extending from the edge of the mesh, particularly where the edge is curved. In other words, the perimeter of the mesh comprises the spaced ends of the fibres or strands and is not smooth. It is thought that the jagged rough nature of the edges of the implant increases the likelihood of extrusion of the edge of the mesh in situ.

Conventional meshes are generally unnecessarily strong and substantial for use in the vaginal wall and of significant mass. This results in an unnecessary excess of foreign body material in the vaginal wall, increasing the risks associated with the placement of foreign bodies inside the human body, such as the risk of infection. Likewise, the bulk of such meshes can undesirably result in discomfort for the patient as the mesh can often be felt when in position. This is of particular concern when a mesh is placed in sensitive vaginal tissues or near to bowel or bladder.

A further disadvantage of the meshes presently used to treat hernias relates to pore size. The pore size of meshes in use is unphysiological and does not encourage acceptance of the implant in the body.

It is a aim of the present invention to overcome problems associated with existing meshes used to treat hernias.

According to the present invention there is provided a surgical implant suitable for treatment of hernias, the implant comprising a mesh having a residual maximum mass density of 50 g/m².

Preferably the maximum mass density is less than 30 g/m². More preferably the maximum mass density is less than 25 g/m².

By minimising mass density of a mesh for use in treating hernias the advantages of using a mesh are still apparant whereas the disadvantages are lessened in that jagged and rough edges are minimised as is the risk of infection. The residual mass density is the mass density of the mesh after implantation.

Preferably the surgical implant mesh comprises strands and includes major spaces and pores.

The strands of the mesh may be formed by at least two filaments, the major spaces formed between the strands providing the surgical implant with the necessary strength, the filaments arranged such that pores are formed in the strands of the mesh.

Alternatively the strands may be formed by monofilaments which form loops which give rise to the pores.

Preferably strands are spaced by wider distance than the fibres or filaments of conventional meshes used in hernia repair.

Preferably the strands are spaced apart to form major spaces of between 1 to 10 mm.

More preferably the strands are spaced apart to form major spaces of between 2 to 8 mm.

The use of mesh having strands spaced between 1 to 10 mm apart has the advantage of reducing the foreign body mass that is implanted in the human body. Only sufficient tensile strength to securely support the defect and tissue being repaired is provided by the mesh.

It is desirable that the mesh of the present invention has a mass of between one tenth (¹⁄₁₀th) and one hundredth (¹⁄₁₀₀th) that of a conventional, e.g. Prolene®, mesh of the same surface area. The mesh of the invention therefore avoids the unnecessary bulk of conventional meshes.

More specifically it is preferred that the mass density is less than 50 g/m², more preferably less than 30 g/m and most preferably less than 20 g/m². It is also preferred that the strands of the mesh of the present invention are narrower than those of meshes of the prior art.

Preferably the strands have a diameter of less than 600 μm.

In one embodiment the strands are arranged to form a diamond net mesh.

In an alternative embodiment the strands are arranged to form a hexagonal net mesh.

The strands and filaments are preferably warp knit.

In an alternative embodiment the strands are arranged to form a net mesh with suitable tensile strength and elasticity.

Preferably the strands are arranged to form a net mesh which has isotropic or near isotropic tensile strength and elasticity.

Preferably the filaments have a diameter of between 0.02 to 0.15 mm.

More preferably the filament of the mesh is of a diameter 0.08 to 0.1 mm.

This likewise has the advantage of reducing the overall bulk of the implant, and hence the amount of material retained in the human body.

Particular meshes which are embodiments of the present invention include warp knit diamond or hexagon net diamond net meshes. Four particular. embodiments are set out below.

In two particular embodiments wherein the filaments are formed from polypropylene having a diameter of 0.07-0.08 mm wherein the strands are spaced to form spaces of either 2 mm or 5 mm.

Alternatively, filaments are formed from polyester having a diameter of 0.09 mm wherein the strands are spaced to form spaces of 5 mm.

Alternatively, filaments are formed from polyester having a diameter of 0.05-0.07 mm wherein the strands are spaced to form spaces of 2 mm.

As the surgical implant is comprised of narrow members arranged to be spaced by relatively wide gaps, major spaces, tissue may be slow to grow into the mesh. It is desirable for the mesh to have means for promoting tissue ingrowth. More specifically, it is desirable to provide pores in the strands of the mesh to aid tissue ingrowth and to which tissue may more easily adhere.

Preferably two filaments are interwoven/knitted to produce strands of the mesh comprising pores.

Alternatively at least three filaments are interwoven/knitted to produce strands of the mesh comprising pores.

For manufacturing reasons it is preferred that two filaments are used to form the pores in the strands of the mesh which aid tissue ingrowth, however if the one filament could be suitably knotted or twisted to form pores of suitable dimensions it is clear that this could be used to similar effect to form the strands of the mesh.

Preferably the pores in the strands are of between 50 to 200 nm in diameter.

More preferably the pores are of between 50 to 75 nm in diameter.

This is important in enabling efficient fibroblast throughgrowth and ordered collagen laydown in order to provide optimal integration into the body. This is discussed in detail in copending Patent Application No PCT/GB01/04554.

Rings or loops of material comprising pores of between 50 to 200 nm may be adhered to or formed on the strands of the mesh to provide pores.

As mentioned above, reducing the mass of the mesh has distinct advantages in relation to the suitability of the mesh for implantation in the body, i.e. the reduction of foreign body mass and improving the comfort of the patient. However, the handling characteristics of such a mesh, e.g. the ease with which a surgeon can manipulate and place the surgical implant in its desired location in the body, can be poor in some circumstances. More specifically, a mesh having narrow members or strands that are widely spaced will inevitably be somewhat flimsy and lacking in rigidity compared to conventional meshes.

Ideally the implant should be formed from materials or uses technologies which provide the implant with Dual Phase Technology, such that it has suitable surgical handling characteristics and is also of minimal mass and suited for implantation in the body. The implant may be formed from a range of materials to provide it with Dual Phase Technology™.

The term Dual Phase Technology™ refers to a means to provide temporary substance to the mesh. Depending on the type of Dual Phase Technology™ employed the benefits imported, in addition to allowing minimal residual mesh mass may include assisting the mesh to be handled and cut, minimizing the effect of rough edges, assisting placing the mesh in position and providing tackiness to assist in holding the mesh in position on implantation, thus minimising or negating the need for any additional fixation by suturing or adhesion.

In a preferred embodiment of the invention having improved handling characteristics, the implant therefore has an absorbable coating. Preferably this coating encapsulates the mesh of the surgical implant.

Alternatively this coating is applied to at least one face of the mesh.

The coating, covering or layer of absorbable material stiffens and adds bulk to the mesh such that it is easier to handle.

As the coating, covering or layer is absorbable, it is absorbed by the body after implantation and does not contribute to the foreign body mass retained in the body. Thus, the advantages of a surgical implant having minimal mass are retained.

Preferably the coating, covering a layer absorbs within 48 hours following implantation.

The coating, covering or layer may comprise any suitable soluble and biocompatible material.

Suitable hydrogel materials can be obtained from First Water in the UK. A typical hydrogel being developed for use in this application is known as FIRST PHASE™ or PHASE 1™.

The absorbable material may be a soluble hydrogel such as gelatin,

Alternatively the absorbable material is a starch or cellulose based hydrogel.

In a further alternative the absorbable material is an alginate.

In a further alternative the absorbable material may contain hyaluronic acid.

The coating, covering or layer may have any thickness or bulk that provides the surgical implant with suitable handling characteristics.

Preferably, the coating is a sheet with a thickness greater than that of the mesh.

Suitable handling characteristics may also be provided to the mesh by a range of other methods. The surgical implant may comprise a mesh and a backing strip the backing strip releasably attachable to the mesh.

The backing strip may be formed from a range of materials including plastics.

The surgical implant may be releasably attachable to the backing strip by adhesive.

The releasable attachment of a backing strip to the mesh provides a more substantial and less flexible surgical implant that is more easily handled by a surgeon. Following suitable placement of the surgical implant the backing strip can be removed from the surgical implant, the surgical implant being retained in the body and the backing material being removed by the surgeon. The surgical implant can therefore benefit from reduced mass while still providing characteristics required for surgical handling.

In a further alternative the strands of the mesh of the surgical implant are comprised of bicomponent microfibres.

Preferably the bicomponent microfibres comprise a core material and surface material.

The composite or biocomponent fibres preferably comprise a nonabsorbable or long lasting absorbable core and a shorter lasting absorbable surface material.

Whereas any licenced materials may be used, suitable materials presently available include polypropylene for the core and polylactic acid or polyglycolic acid for the surface materials.

Alternatively the bicomponent microfibres comprise an material which is rapidly absorbed by the body and a material which is not absorbed for a suitable longer period of time.

Preferably the surface material is capable of being absorbed by the body in a period of less than 48 hours.

Preferably the core material is capable of remaining in the body for a period of time sufficient to enable tissue ingrowth.

The surface material of the bicomponent microfibres or a portion of the composite polymers present during the insertion and placement of the surgical implant provides the surgical implant with characteristics required for surgical handling.

Following a period of insertion in the body, the surface material of the bicomponent microfibre is absorbed by the body leaving behind the reduced foreign mass of the core material of the strands of the mesh.

It is preferred that the surface material of the bicomponent microfibre is absorbed by the body within a number of hours such that only a core portion is left in the body for an extended length of time. Typically materials presently available which could be used to form the microfibres are absorbed by the body over a period of days or weeks.

The filaments of the mesh comprise a plastics or synthetic material.

Preferably the filaments of the mesh comprise of polypropylene or polyester.

Alternatively the filaments of the mesh comprise an absorbable material.

It can be appreciated that filaments which comprise in part of absorbable material would allow better surgical handling, but would enable the implant to also have minimal mass following implantation in the body.

Preferably the surgical implant comprises material that has memory.

Preferably the surgical implant has memory which urges the surgical implant to adopts a flat conformation.

Preferably the implant has a generally curved perimeter, i.e. to have few or no corners or apexes, as sharp corners increase the likelihood of edge erosion and infection. The specific shape will, however, vary according to the use to which the implant is to be put.

Due to the variety of sizes of such defects, and of the various fascia that may need repair by the implant, the implant may have any suitable size, Preferably the surgical implant is of width between 1 cm to 10 cm and of length between 1 cm to 10 cm.

It may be desirable to provide a variety of implants having different sizes in order that a surgeon can select an implant of suitable size to treat a particular patient. This allows implants to be completely formed before delivery, ensuring, for example, that the smooth edge is properly formed under the control of the manufacturer. The surgeon would have a variety of differently sized (and/or shaped) implants to hand and select the appropriate implant to use after assessment of the patient.

Typically an anterior uterovaginal prolapse is ellipse shaped or a truncated ellipse whereas a posterior prolapse is circular or ovoid in shape.

Accordingly the implant shape may be any one of elliptical or tuncated ellipse, round, circular, oval, ovoid or some similar shape to be used depending on the hernia or polapse to be treated.

Different shapes are suitable for repairing different defects in fascial tissue and thus by providing a surgical implant which can be cut to a range of shapes a wide range of defects in fascial tissue can be treated.

Preferably the mesh can be cut to any desired size. The cutting may be carried out by a surgeon or nurse under sterile conditions such that the surgeon need not have many differently sized implants to hand, but can simply cut a mesh to the desired size of the implant after assessment of the patient. In other words, the implant may be supplied in a large size and be capable of being cut to a smaller size, as desired.

In this regard, whilst the surgical implant of the invention is particularly useful for the repair of uterovaginal prolapse, it may be used in a variety of surgical procedures including the repair of hernias.

Preferably the surgical implant is suitable for use in the treatment of hernias including incisional and inguinal hernias and/or for the treatment of uterovaginal prolapse.

More broadly, the Applicant has therefore recognised that the implant can have any shape that conforms with an anatomical surface of the human or animal body that may be subject to a defect to be repaired by the implant.

As discussed a disadvantage of the meshes used in hernia repair is that they have jagged or rough edges. Due to the wide spacing between strands of the mesh described above and the small diameter of the filaments, the edge problems are mitigated to an extent by the present invention.

To further reduce edge problems it would be preferable if a mesh had a circumferential member which extends, in use, along at least part of the perimeter of the implant to provide a substantially smooth edge.

In other words, the mesh has at least one circumferential member (i.e. fibre, strand or such like) that extends around at least part of its circumference.

Preferably at least part of the perimeter of the implant is defined by the circumferential member, Alternatively at least part of the perimeter of the implant is defined by more than one circumferential member, at the edge of the mesh.

The edge of the mesh, and hence the perimeter of the implant, can therefore be generally smooth and this has significant advantages over conventional surgical meshes. Specifically, the Applicant has recognised that an implant having a smooth edge is less likely to cause edge extrusion or erosion.

Any amount of the perimeter of the implant may be defined by the circumferential member(s).

However, in order to maximise the benefits of the implant of the invention, it is preferable that at least 50% of the perimeter of the implant is defined by the circumferential member(s).

More preferably at least 80% of the perimeter of the implant is defined by the circumferential member(s).

Most preferably 100% of the perimeter of the implant is defined by the circumferential member(s).

The majority or the whole of the perimeter of the mesh being smooth minimises the risk of a rough edge causing edge erosion or infection.

The circumferential member(s) may be arranged in one of a variety of ways to provide the smooth edge or perimeter.

Preferably the circumferential members are arranged such that they each follow the edge of a desired shape of the surgical implant, the perimeter of the implant formed from as few members as possible.

This simplifies the construction of the mesh, which is desirable not only for manufacture, but also because simpler structures are less likely to have defects which might be problematic after implantation.

Preferably the perimeter of the mesh is defined, in use, by one circumferential member.

Preferably the mesh has a plurality of circumferential members arranged at different radial locations.

In order to provide an implant of given dimensions, the periphery of the mesh outward of the desired circumferential member is cut away such that one or more selected circumferential members form the perimeter of the implant as desired.

More preferably, the circumferential members are arranged concentrically.

A concentric arrangement of a plurailty of circumferential members conveniently allows maintenance of the shape of the implant for different sizes of implant and provides the mesh with an even structure.

The remainder of the structure of the mesh may take a variety of forms.

The circumferential members can be arranged to join with one another in order to form an integral mesh.

Alternatively the mesh may additionally comprise transverse members which extend across the circumferential members joining the circumferential members.

The transverse members may extend radially from a central point to the perimeter of the implant.

Alternatively, the transverse members may extend toward the perimeter of the implant.

Preferably the transverse members are arranged to provide substantially even structural strength and rigidity to the implant.

It may be desirable to secure the mesh in place once it has been suitably located in the patient.

Preferably the mesh can be sutured to strong lateral tissue.

Alternatively, the mesh may be glued in place using a biocompatible glue.

This is advantageous, as it is fairly quick to apply glue to the area around the surgical implant.

Preferably the mesh comprises at least one capsule containing biocompatible glue for securing the implant in place.

Preferably 4 capsules containing glue are provided around the perimeter of the surgical implant.

Preferably the capsules comprise hollow thin walled spheres of around 3 to 5 mm diameter including gelatin.

Preferably the glue is a cyanoacrylate glue.

Conventionally, open procedures have been preferred for the treatment of hernias with meshes, as relatively broad access is required to the site of the defect to suitably implant and secure a mesh by sutures or such like.

However, it is desirable to treat hernias, as when carrying out any surgery, with as little trauma to the patient as possible. Thus, the use of minimally invasive techniques has been suggested for the treatment of hernias. However, such surgical techniques have not been considered to be useful in the treatment of uterovaginal prolapse with a mesh, as it has not been considered practical to position a mesh subcutaneously in the vaginal wall due to the difficulty in gaining direct access to this area.

According to another aspect of the present invention, there is provided a minimally invasive method of treating uterovaginal prolapse, the method comprising the steps;

making an incision in the vaginal wall close to the opening of the vaginal cavity and, making a subcutaneous cut, through the incision, over and surrounding the area of the prolapse, which cut is substantially parallel to the vaginal wall; and inserting a mesh according to the present invention, through the incision, into the space defined by the cut.

Thus, a mesh or the surgical implant such as that according to the invention can be inserted through a small incision (e.g. around 1 cm to 2 cm in length) at or in the region of the periphery or opening of the vaginal cavity. An incision in this position is easier for a surgeon to access than an incision deeper in the vaginal cavity, yet the Applicant has realised that it is also convenient to treat vaginal prolapse by implanting a mesh in a surgical procedure carried out entirely through such an incision.

Preferably, the incision is at the anterior or posterior extremity of the prolapse sac of the vaginal cavity.

This is desirable as prolapse most often occurs in the anterior or posterior vaginal wall, so positioning the incision in such a location allows the most convenient access to these parts of the vaginal wall.

The provision of suitable handling characteristics for the mesh is particularly advantageous when the mesh is intended to be used in a conventional open surgical procedure, as the surgeon needs to handle the implant directly in order to place it in its desired location.

However, the suitable placement particularly in the treatment of uterovaginal prolapse, by minimally invasive techniques require the mesh to be as flexible as possible and therefore to have no absorbable coating or encasement.

A flexible, less bulky mesh may be more easily handled by tools that may be used to carry out the procedure.

Tools that may be used to carry out this procedure have a number of specific needs that need to be met that are not presently met by conventional minimally invasive surgical tools.

These specific needs can best be understood by considering the steps of the surgical procedure of the invention in turn.

The incision is made in the vaginal wall at the opening of the vaginal cavity. This can be carried out using a conventional implement such as a scalpel. It is preferable that the incision is as small as possible as this reduces trauma to the patient.

A cut is then made in the vaginal wall over the defect causing the prolapse or hernia. For example, scissors or another specialised cutting tool can be inserted through the incision and manipulated to provide a cut over the defect. The cut is below the surface of the skin and may provide a space between an upper (or outer) layer and a lower (or inner) layer of the vaginal wall, or between the skin and the vaginal wall, in the region of the defect, into which cavity the mesh can be inserted.

Next, the mesh is placed in the space defined by the cut. It is preferred that the mesh of the invention is supplied rolled up in order that it can be inserted through a small incision and unfurled in situ, i.e. in its intended position. Thus, it may be possible for the surgeon to insert the mesh through the incision by hand. However, this is likely to result in the incision needing to be large enough for the surgeon to insert a finger to manipulate the mesh in the space. This may cause unnecessary trauma to the patient and can be difficult for a surgeon to carry out.

According to another aspect of the present invention, there is provided a surgical tool for delivering a mesh subcutaneously through an incision, the tool being adapted to radially confine the mesh during delivery and being operable to release the mesh in its intended position.

Such a tool for placement of a mesh or the surgical implant of the present invention can insert and position the mesh or surgical implant in a convenient and controlled manner through a small incision. Furthermore, the incision through which the mesh is inserted need only be as large as the diameter of the tool, or the tool when carrying the mesh, which can be significantly smaller than where a surgeon's finger must be able to fit through the incision.

Preferably the tool comprises a housing and unfurling means the housing and unfurling means insertable through an incision in the patient, the housing and unfurling means adapted to accommodate a rolled up mesh and separable to release the mesh the unfurling means capable of unfurling the rolled up mesh without any significant movement around the area of the incision.

Preferably, the tool comprises two or more parts, the parts movable such that in a first position they house the mesh or surgical implant and, in a second position the mesh or surgical implant is released. More preferably the tool comprises two semi-circular channels, an inner channel having an external diameter suitable for fitting inside an outer channel.

The channels may be rotatable about a common axis such that in a first position the open faces of the channels face one another to form a closed housing and in a second position the inner channel sits inside the other channel to release the mesh.

Alternative the tool comprises a shaft and releasable securing means, the shaft adapted such that the mesh can be rolled around the shaft and releasable securing means to secure the rolled mesh in place.

In use, the tool is inserted through the incision with the mesh rolled around the outside of the shaft. Once the tool has been inserted, the mesh is released by turning the shaft to unroll the mesh at the same time as moving the shaft across the space in which the mesh is being placed.

A needle may be used to secure the free, outer end of the mesh whilst it is unfurled. The needle may be inserted through the vaginal wall to pin the mesh in place. Similarly, where the mesh is released from within a housing, needles may be used to ease the mesh out of the open housing.

In an alternate embodiment, the tool comprises two or more arms, each of which is releasably attached at one end to an edge of the surgical implant. The arms may be movable from a first position in which they radially confine the mesh to a second position to unfurl the mesh in its intended position.

In one example, the arms are pivotally interconnected such that they can be manipulated to move the ends of the arms from the first position to the second position.

In another example the arms may be arranged to extend radially outward from a housing to move from the first position to the second position. The extendable arms may comprise wires arranged to be extendable and retractable from and into the housing by operation at an end of the housing.

In another example, the arms may be resilient or sprung elements that can be released from the first position and move into the second position to which they are biased, i.e. to unfurl the mesh.

As can be appreciated, all of the above, embodiments of the tool are able to unfurl the mesh without any significant movement around area of the incision. For example, the pivot can be arranged to coincide with the incision, the tool rolled around an arc centred at the incision or the arms operated or housing opened forward of the incision. Thus, the incision can be small as no lateral movement is required at the area of the incision.

Embodiments of the present invention will now be described, by way of example only, with reference to the accompanying drawings, in which.

Figure 10:
Figure 11:
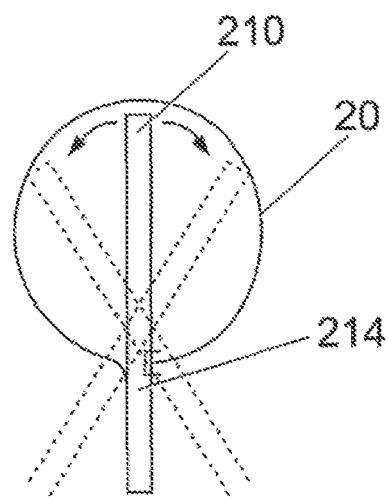
Figure 12:
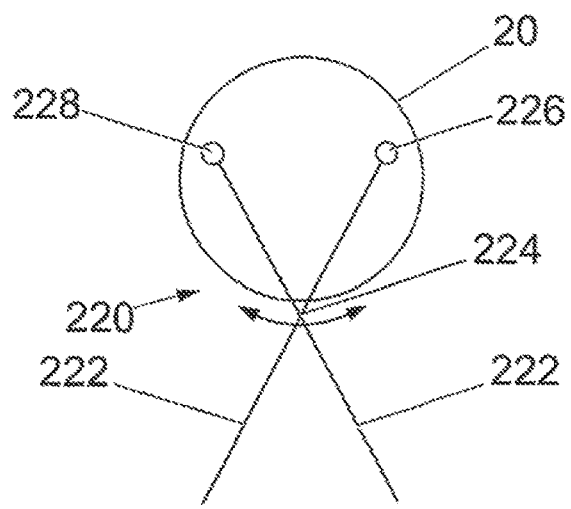

FIGS. 9a, 9b 9c and 9d illustrate surgical implants according to the invention having a third shape;

FIG. 10 illustrates a first surgical tool according to the invention in cross-section;

FIG. 11 illustrates a second surgical tool according to the invention;

FIG. 12 illustrates a third surgical tool according to the invention; and

Figure 13:
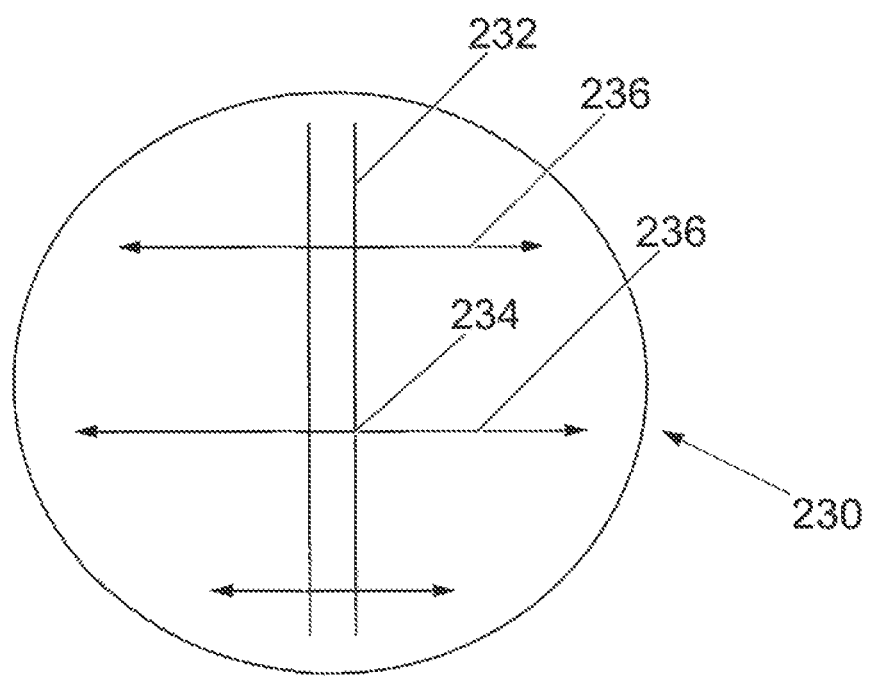

FIG. 13 illustrates a fourth surgical tool according to the invention.

Figure 1:
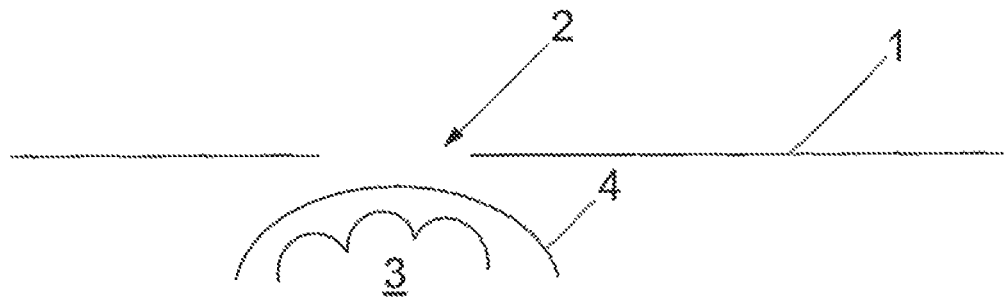
FIG. 1 is an illustration of a hernia.
Figure 2:
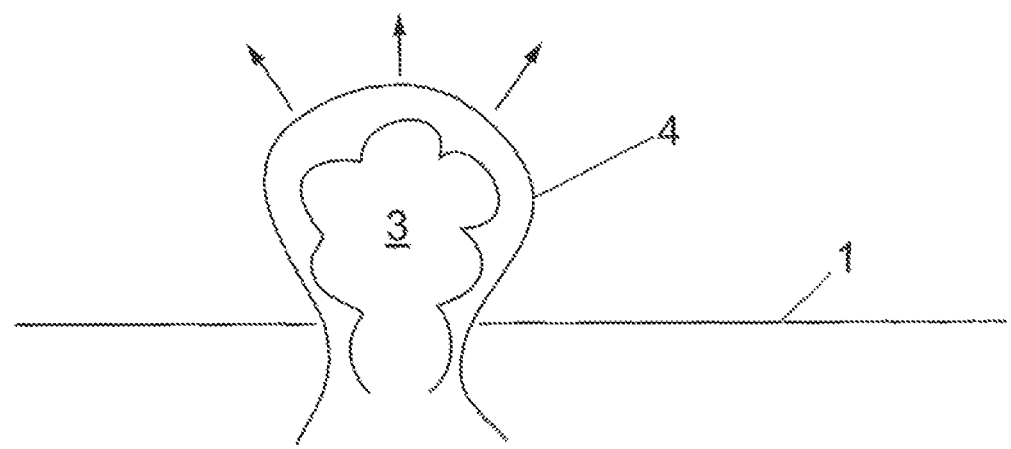
FIG. 2 is an illustration of the hernia of FIG. 1 when intra-abdominal pressure is raised.

Referring to FIGS. 1 and 2, a hernia, vaginal prolapse or such like occurs when a fascial wall 1 ruptures, forming a defect 2, i.e. a weakening or, in this case, parting of the fascial wall 1. An organ 3, contained by the fascial wall 1 is then able to protrude through the defect 2. Such protrusion is illustrated in FIG. 2 and occurs particularly when pressure within the cavity defined by the fascial wall 1 is raised. For example, in the case of an inguinal hernia, when a patient coughs, intra-abdominal pressure is raised and the intestines may be pushed through the defect 2 in the abdominal wall.

Whilst the organ 3 that may protrude through the defect 2 is usually still contained by some other membrane 4, the hernia, prolapse or such like is inevitably painful and liable to infection or other complications. An effective and desirable treatment is therefore to close the defect 2 and contain the organ 3 in its normal position.

Figure 3:
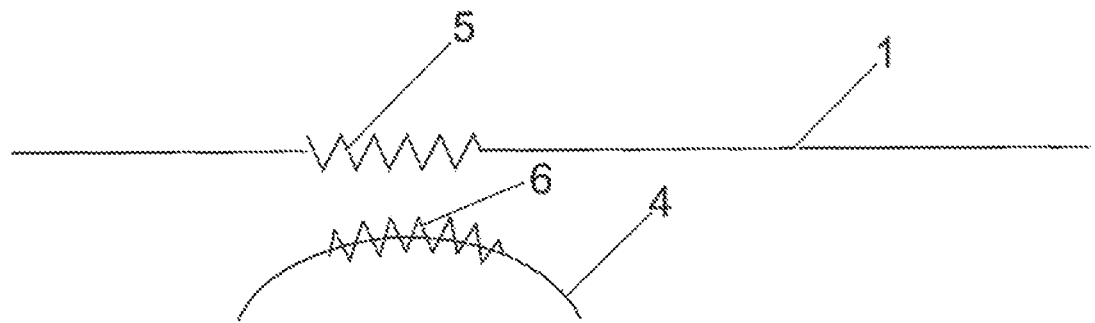
FIG. 3 is an illustration of the hernia of FIG. 1 after repair in accordance with the prior art.

Referring to FIG. 3, hernias, vaginal prolapse and such like are conventionally repaired by providing sutures 5 across the defect 2 to join the tissues of the fascial wall 1. In addition, it may be firstly necessary to plicate (i.e. fold or reduce) the membrane 4 as this may have stretched due to distention of the organ. 3. Plication of the membrane 4 corrects the stretching and helps to relieve pressure on the area of the defect 2 during healing as the membrane 4 can act to contain the organ 3 to some extent. Plication is generally achieved by applying sutures 6 to the membrane 4.

Figure 4:
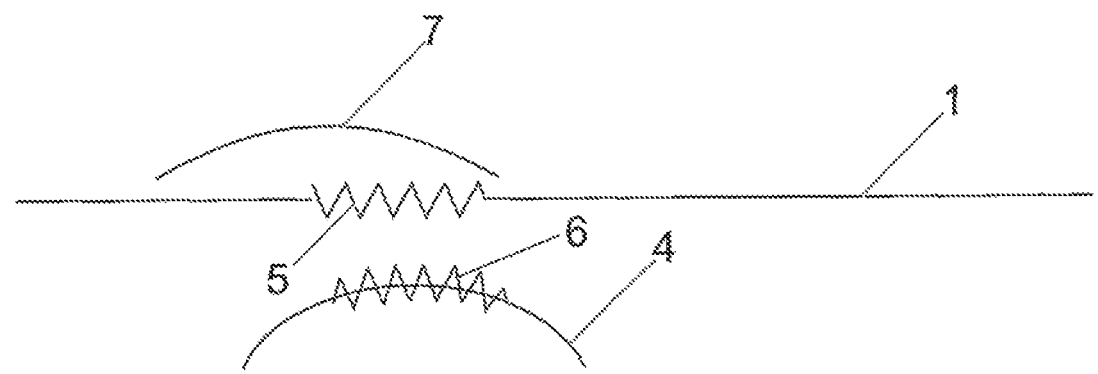
FIG. 4 is an illustration of the hernia of FIG. 1 after an alternate repair in accordance with the prior art.

Referring to FIG. 4, it is also a known method of treating hernias to provide, additionally or alternatively to sutures, a mesh 7 across the defect 4. This allows for the defect 2 to be repaired without the parted tissues of the fascial wall 1 necessarily being brought together and for the defect to heal without the fascial wall 1 being pinched or tensioned to correct the defect 2.

Figure 5:
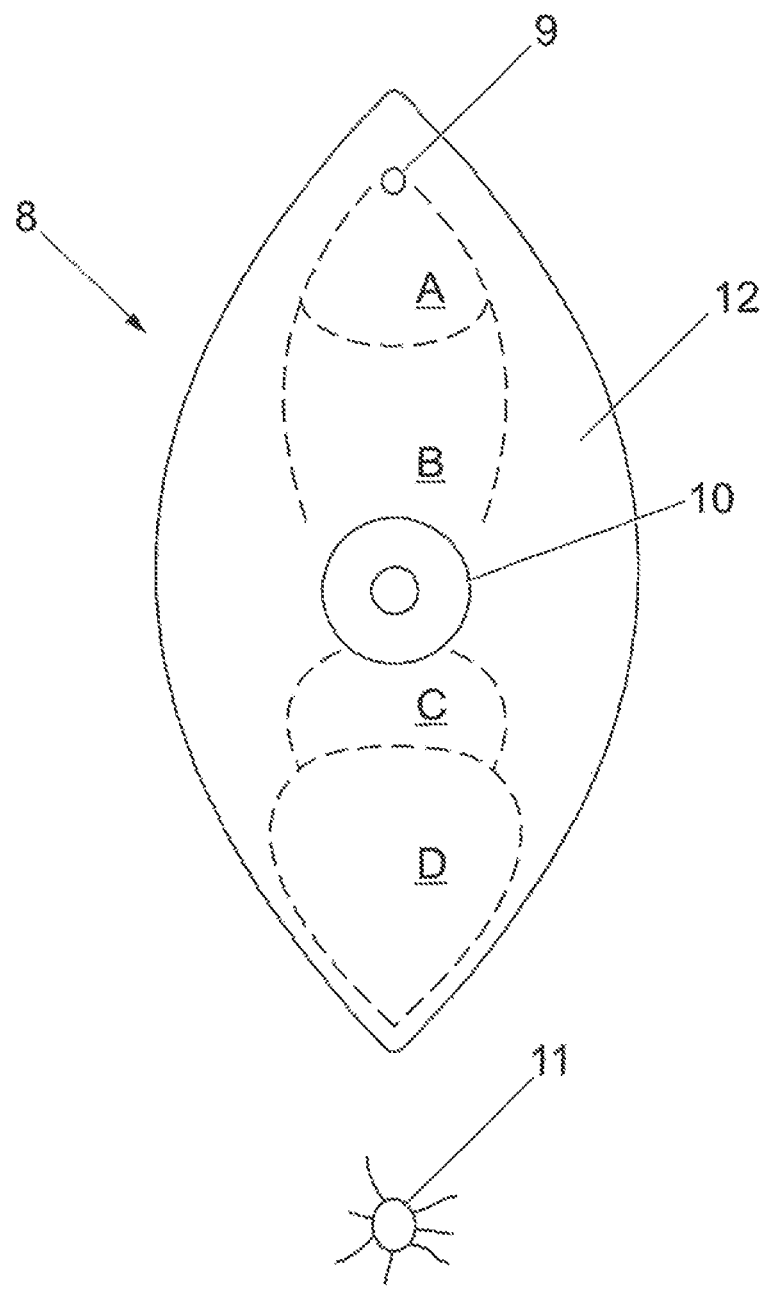
FIG. 5 is a schematic illustration of the female human vaginal area.

FIG. 5 schematically illustrates (a sagittal view of) the female human vaginal area. The vagina 8 is illustrated with its anterior portion (front) at the top of the diagram and the posterior portion (rear) at the bottom of the diagram. The opening of the urethra, or urethral meatus, 9 is at the forward or anterior end of the vagina 8. The central portion of the vagina 8 forms the vaginal cavity which terminates at the cervix 10. Spaced from the rearward or posterior end of the vagina 8 is the anus 11. Four areas A to D of the vaginal wall 12 are outlined in FIG. 5. These areas A to D are those areas of the vaginal wall 12 in which vaginal prolapse often occurs.

Figure 6:
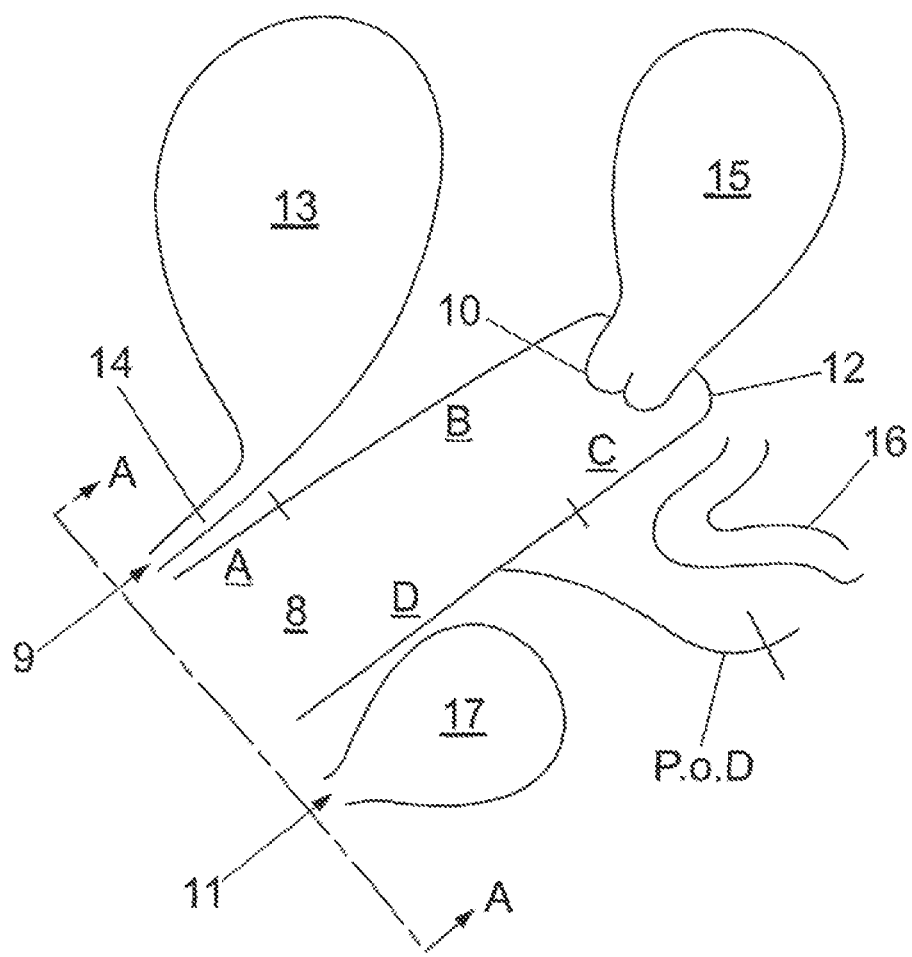
FIG. 6 is a cross-sectional view of the female human vaginal area along the line A-A of FIG. 5.

Referring to FIG. 6, which is a cross sectional view along the line A-A in FIG. 5, it can be more clearly seen that the wall 12 of the vagina 8 is bounded by the bladder 13 and urethra 14, the uterus 15, the small bowel 16 and rectum 17. The small bowel 16 and rectum 17 are separated by the "Pouch of Douglas" PoD.

Area A is the lower one third of the anterior vaginal wall 12 (i.e. the one third nearest the entrance to the vaginal cavity) adjacent the bladder 13 and urethra 14. Prolapse in this area is referred to as anterior or, more specifically, urethracoele prolapse. Area B is the upper two thirds of the anterior vaginal wall 12. Prolapse in this area is referred to as anterior or, more specifically; cystocoele prolapse. The central area of the vaginal wall 12 in which the cervix 10 is located is adjacent the uterus 15 and prolapse in this area is referred to as central, uterine or vault prolapse. Area C is the upper one third of the posterior vaginal wall 12. This area of the vaginal wall 12 is adjacent the small bowel 16 and prolapse in this area is referred to as posterior or entreocoele prolapse. Finally, area D is the lower two thirds of the posterior vaginal wall and is adjacent the rectum 17. Prolapse in this area is generally referred to as posterior or rectocoele prolapse.

Conventionally, any of the above types of hernia have been treated by providing sutures in the area of the prolapse. For example, the extent of the defect causing the prolapse is first identified by the surgeon. Lateral sutures, i.e. sutures from one side to the other of the vaginal wall 12 as seen in FIG. 5 or right to left rather than anterior to posterior, are provided across the area of the defect. This joins the parted tissues of the vaginal wall and repairs the defect. The organ protruding through the vaginal wall is therefore contained. Disadvantages of this technique include anatomical distortion of the vagina due to tensioning of the wall by the sutures to repair the defect.

A surgical implant for use in the repair of vaginal prolapse in accordance with an embodiment of the present invention comprises a mesh 20. The mesh is comprised of strands 22. The strands being less than 600 µm and approximately 150 to 600 µm in diameter. The strands are arranged such that they form a regular network and are spaced apart from each other such that for a diamond net a space of between 2 mm to 5 mm exists between the points where the strands of the mesh interact with each other (a). In a hexagonal net arrangement the space is between 2 mm to 5 mm between opposite diagonal points where the strands of the mesh interact (b).

It is preferable to space the strands as far as part as possible to allow blood to pass through the implant and reduce the mass of the implant, while providing the mesh with sufficient tensile strength and elasticity to be effective. It can therefore be appreciated that considerable variability in the maximum spacing between the strands can be achieved depending of the material from with the strands are comprised and the net pattern in which the strands are arranged.

Figure 7A:
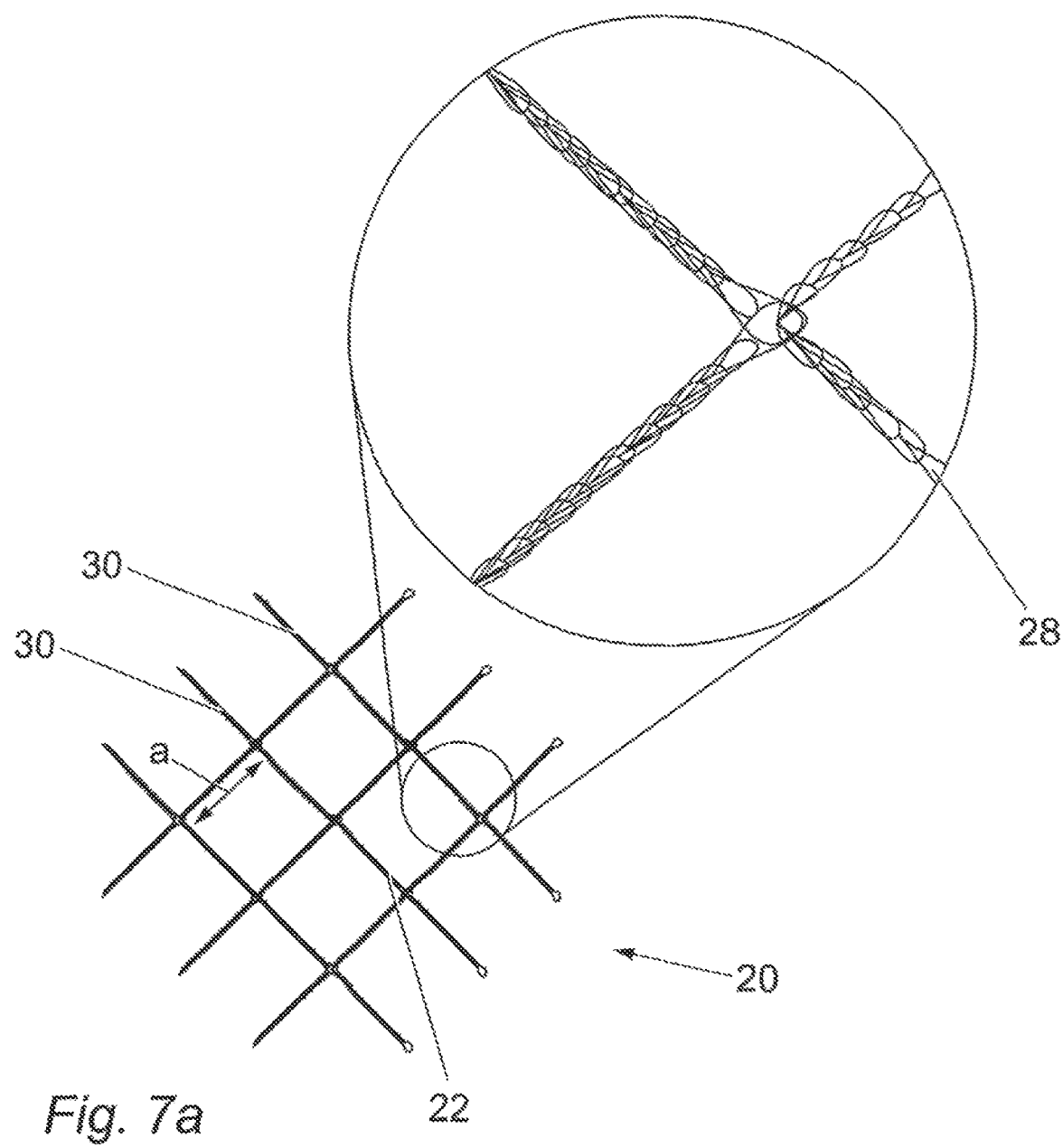
FIGS. 7a and 7b illustrate surgical implants according to the invention having a first shape.

In the embodiment shown in FIG. 7a the strands are arranged in a diamond net pattern 24, however any pattern which provides suitable tensile strength an elasticity may be used.

Figure 7B:
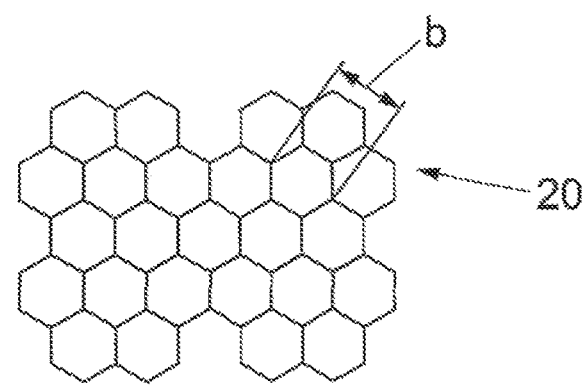

For example a hexagonal net pattern may be used as shown in FIG. 7b.

Ideally in order to reduce the overall mass of the implant the strands 22 should have as narrow a diameter as possible while still providing the mesh 20 with suitable tensile strength and elasticity.

The strands 22 of the mesh 20 are comprised of at least two filaments 26 arranged to interact such that pores 28 are formed between the filaments 26.

The pores 28 formed between the filaments 26 are around 50 to 200 µm, such a spacing allowing fibroblast through growth to occur. This fibroblast through growth secures the implant 20 in place within the body. Additionally and importantly the suitably sized pores allow the implant 20 to act as a scaffold to encourage the lay down of new tissue. The lay down of new tissue promotes the healing of the hernia.

The filaments 26 may be formed from any biocompatible material. In this embodiment the filaments 26 are formed from polyester, wherein each polyester filament 26 is around 0.09 mm in diameter.

In the embodiment shown the filaments 26 of the strands 24 are knitted together using warp knit to reduce the possibility of fraying of the filaments 26 and strands 24.

Alternative suitable materials of which the filaments may be formed include polypropylene.

Suitable materials from which the mesh can be made: provide sufficient tensile strength to support a fascial wall during repair of a defect in the fascial wall causing a hernia; are sufficiently inert to avoid foreign body reactions when retained in the human body for long periods of time; can be easily sterilised to prevent the introduction of infection when the mesh is implanted in the human body; and have suitably easy handling characteristics for placement in the desired location in the body.

The fine warp knit of the filaments 26 provides a surgical implant which is flexible in handing, which can be easily cut into different shapes and dimensions. As the strands 24 are formed using warp knit the possibility of fraying of the edge of the surgical implant 20 following production or cutting of the surgical implant 20 is reduced.

Other methods of reducing fraying of the filaments 24, not arranged to form the strands using warp knit, following cutting or production of the implant are heat treatment, laser treatment or the like to seal the edges of the surgical implant.

The mesh 20 may be supplied in any shape or size and cut to the appropriate dimensions as required by the surgeon.

It can be appreciated that cutting of the mesh will produce an unfinished edge 30. Due to the sparse nature of the strands that form the mesh and their narrow diameter this unfinished edge does not suffer from the same problems as edges of meshes of the prior art.

In other words the edge produced is not rough and jagged such that it increases the likelihood of extrusion of the edge of the mesh in situ or the chance of infection.

As discussed an advantage of the mesh of the present invention is that it allows the production of a mesh suitable for use in hernia repair which allows substantially less foreign material to be left into the body.

Figure 8A:
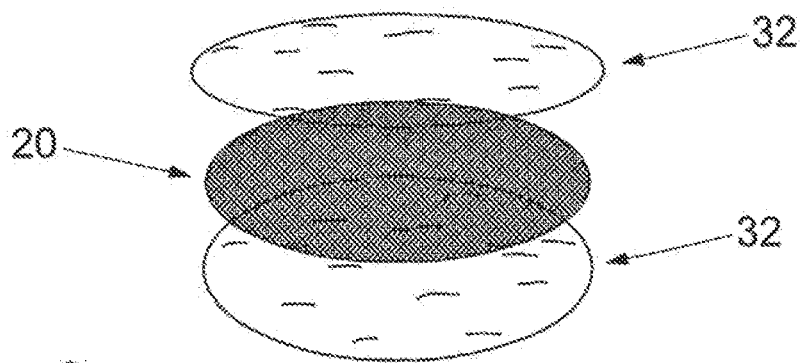
FIGS. 8a, 8b, 8c and 8d illustrate surgical implants according to the invention having a second shape.
Figure 8B:
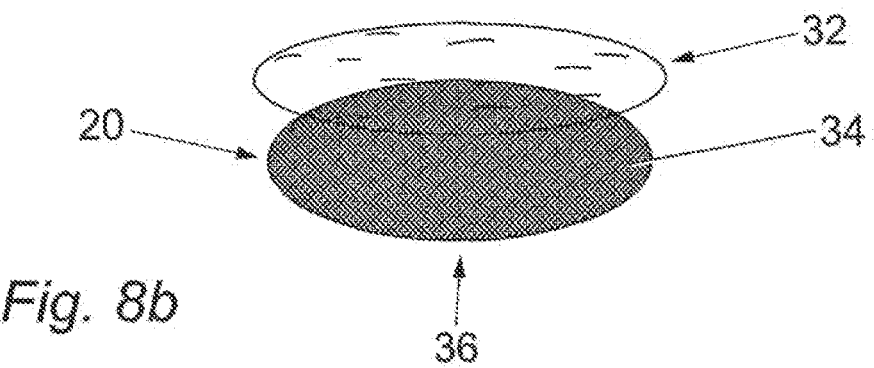

However, the mesh being flexible and insubstantial is less suitable for allowing easy handling of the mesh directly by a surgeon. Referring to FIGS. 8a and 8b the mesh described above may be treatable using an absorbable coating 32.

The absorbable coating 32 comprises a layer of absorbable material having a thickness greater than that of the strands 22 of the mesh 20. For example, the thickness of the layer of absorbable material may be around 1 to 2 mm. The strands 22 of the mesh 20 may be entirely embedded in the absorbable coating 32 such that the outer surface of the mesh 20 is covered entirely of the absorbable coating 32.

In effect the entire surgical implant is encased in the absorbable coating as shown in FIG. 8b.

Thus, the surgical implant has no gaps or holes on its surface. This has the advantage of reducing the likelihood of bacteria becoming lodged on the strands 22 of the mesh 20 before implantation of the mesh 20. Furthermore, the absorbable coating 32 makes the mesh 20 more substantial and less flexible such that it is more easily handled by a surgeon. This is particularly useful when it is desired to place the mesh in a desired location in a conventional, open surgical procedure.

In an alternative embodiment shown in FIG. 8a the absorbable coating 32 comprises a layer of absorbable material applied to one face 34 of the mesh 20, such that the mesh has a first face 34 on which the absorbable material has been applied and a second face 36 on which the absorbable material has not been applied such that the first and second faces 34 and 36 each have different characteristics.

Figure 8C:
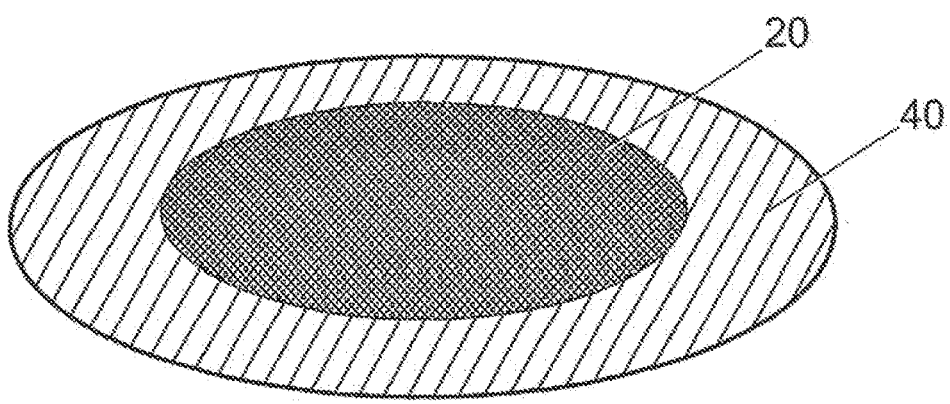

It can also be envisaged that the surgical implant is provided with improved surgical handling qualities by a range of other methods. Such methods including, the releasable attachment of the mesh 20 to a backing strip 40. This embodiment is shown in FIG. 8c.

The backing strip may be formed from plastics material and is adhered to the surgical implant using releasable adhesive.

In a similar fashion to the absorbable coating the backing strip 40 causes the mesh 20 to be more substantial and less flexible such that it is more easily handled by a surgeon. Following the suitable placement of the mesh 20 the backing strip 40 can be removed from the mesh 20, the mesh 20 being retained in the body and the backing material 40 being removed by the surgeon. Application of the backing strip 40 to the mesh 20 means the mesh 20 benefits from reduced mass but that the mesh 20 and backing strip 40 together give characteristics required for surgical handling.

In a further embodiment the filaments of the mesh may be comprised from bicomponent microfibres 50 or composite polymers 60. These technologies provide the implant with dual phase technology.

Figure 8D:
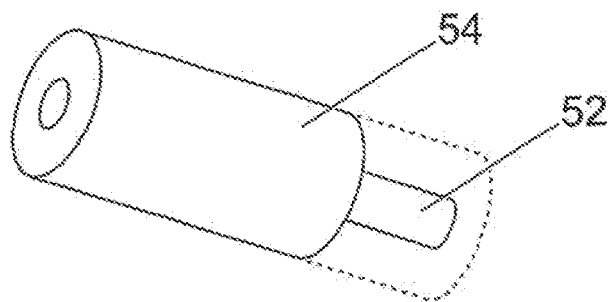

As shown in FIG. 8d the bicomponent microfibres 50 comprise a core 52 (cutaway section shows core region) and surface material 54. The surface material 54 is designed such that it is absorbed by the body in a matter of hours, while the core material 52 remains in the body for a longer period to enable tissue ingrowth.

Suitable bicomponent microfibres 50 include a polypropelene non absorable portion and a polylactic acid absorbable portion.

The surface material 54 is present during the surgical procedure when the mesh 20 is being inserted and located in the patient, and provides the mesh with characteristics desirable for surgical handling. Following a period of insertion in the body, typically a few hours, the surface material 54 is absorbed into the body leaving only the core material 52 of the filaments 26 in the body. The core material of the filament having reduced foreign mass in comparison to meshes of the prior art or the mesh 20 when it also includes the surface material 54.

As shown in FIG. 8e the mesh of the surgical implant may be formed composite polymers 60. As described for the bicomponent microfibres 50, composite polymers 60 provide the surgical implant with dual phase technology. A first face 62 of the mesh 20 thus having particular characteristics such as flexibility and elasticity, while a second face 64 of the mesh 20 provides the mesh 20 with characteristics which improved the surgical handling of the mesh 20 such as strength and robustness. The cutting of the mesh described causes an unfinished edge of the mesh to be produced. This unfinished mesh not being as likely to cause the same problems as the rough and jagged edges of the implants of the prior art, due to the fewer strands, smaller diameter filaments and treatment of the mesh with absorbable coating which protects the tissue from the mesh during the surgical procedure when damage is most likely to occur.

Referring to 9a, a further embodiment of the mesh may comprise strands as discussed and more specifically, perimeter strands. Typically the mesh is circular or the like in shape and thus this perimeter strand can be generally referred to as a circumferential strand 70.

Figure 9A:
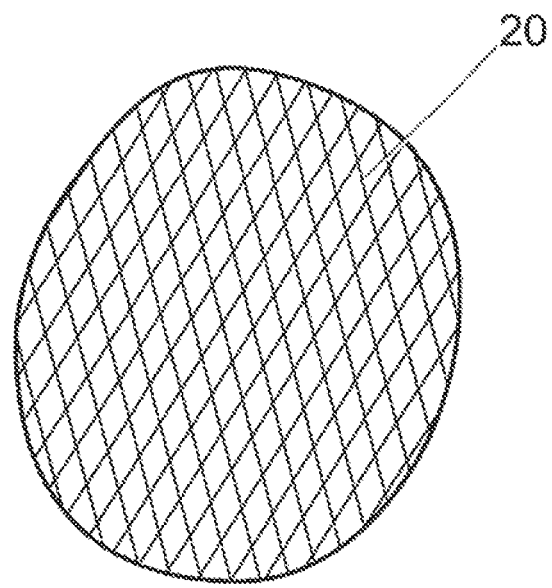

In the example shown in FIG. 9a one strand runs around the circumference of the oval shape of the mesh 20. In another embodiment, several circumferential strands 70 may be present, each circumferential strand 70 may extend over one side of the oval mesh 20, i.e. around half the circumference of the mesh.

Figure 9B:
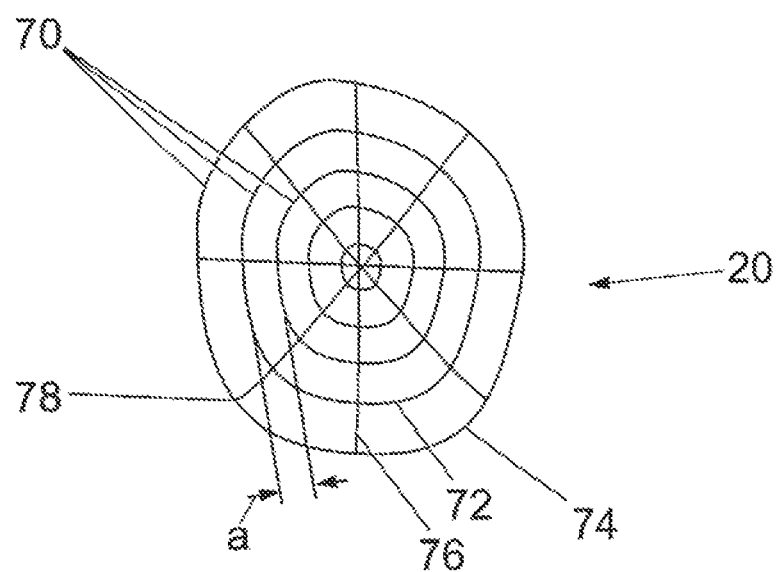

As shown in FIG. 9b the circumferential strands 70 are arranged concentrically and each extends around the mesh 20 at a different radial location.

An outer circumferential strand 70 extending around the perimeter of the mesh 20, and further circumferential strands 72 and 74 are arranged inwardly of the outer circumferential strand forming a perimeter spaced by a distance (a). The distance a between adjacent circumferential members 70, 72 and 74, can vary and in this example is 20 mm.

Transverse strands 76 extend from the centre of the oval mesh 20 to points on the perimeter of the mesh 78. In this example, four transverse strands 76 are provided across the diameter of the mesh 20, dividing the mesh 18 into eight angularly equal portions.

The mesh 20 of this embodiment may be formed from materials as previously described. Depending on the material chosen the mesh may be woven, knitted or extruded as one piece, or individual or groups of strands can be extruded separately and joined to one another.

Figure 9C:
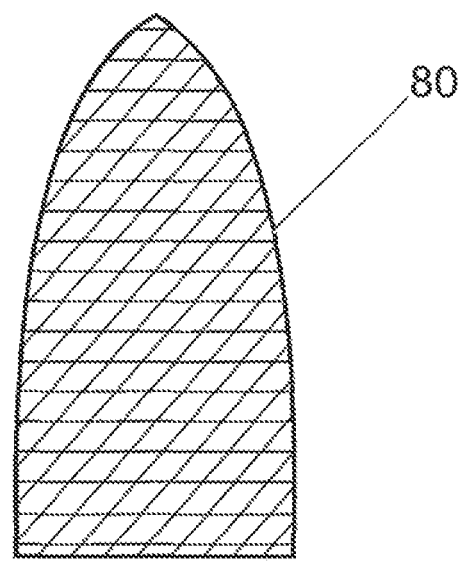
Figure 9D:
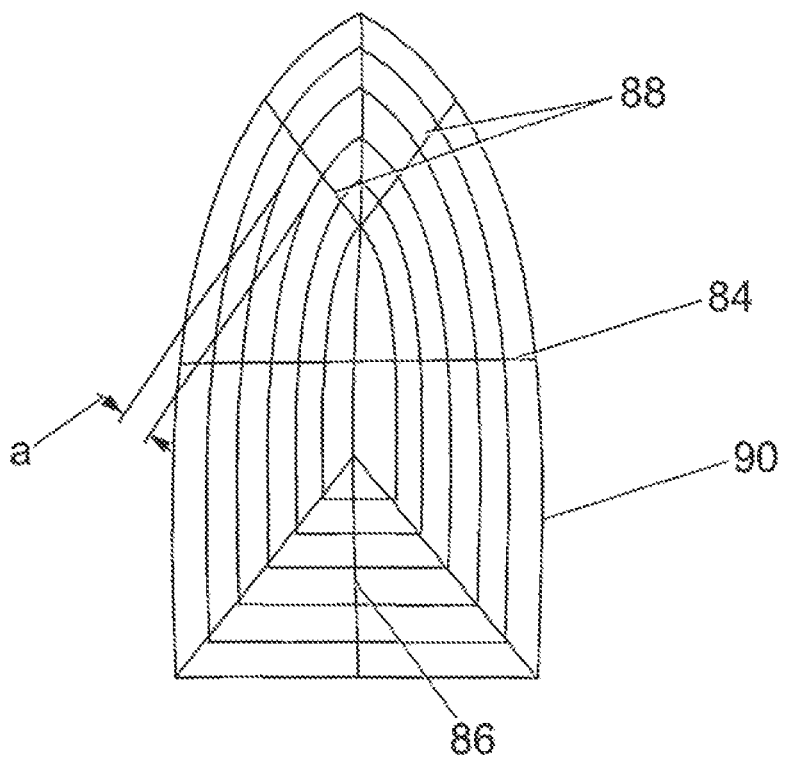

Such a construction as described above provides a mesh 20 with sufficient tensile strength to repair defects causing vaginal prolapse whilst having minimal bulk. Similarly, such a construction provides a suitably flexible yet resilient mesh for handling using the surgical tools described below. Referring to FIGS. 9c and 9d, meshes 80, 82 of in the shape of the outline having angled sides respectively, rather than oval, are illustrated.

These meshes have a similar structure to that described with reference to FIGS. 9a and b. However, the mesh has a perimeter member 80 having angled sides. Further it may have transverse members arranged only to extend towards the perimeter of the mesh, rather than all being across the diameter of the mesh. This provides a more uniform structure. More specifically, referring to FIG. 9d the mesh has a transverse member 84 extending along its axis of symmetry, a transverse member 86 bisecting the axis of symmetry, and four further transverse members 88 extending from the axis of symmetry to the perimeter of the mesh 90.

In addition to the pores provided by the combination of filaments 26 which form the strands 22, pores can be provided by rings of polypropylene positioned at the intersection of the circumferential and transverse members.

Alternatively the pores may be formed by the spacing of the transverse members, such that pores of a size 50-200 µm suitable for enabling tissue ingrowth exist between the transverse members.

To secure the mesh to a suitable location in the body a number of methods can be used. The tackiness of the absorbable coating may hold the mesh suitably until it is secured by tissue ingrowth.

Alternatively the surgical implant can have capsules 100 (not shown) of biocompatible glue for securing the mesh 20 in place. In this example, six capsules 100 comprising spheres having a diameter of 4 mm and made from a rapidly absorbable material are provided around the perimeter of the mesh 20. On placement in the body, the capsules 100 dissolve and release a biocompatible glue contained within to secure the mesh 20 in place.

Referring to FIG. 10, a tool 200 for inserting one of the meshes described (usually without an absorbable coating 32) comprises two channels 202, 204. The channels 202, 204 are semi-circular in cross-section and the channel 202 has a diameter slightly smaller than the diameter of channel 204. The channels are interconnected such that the channel 202 can be rotated inside the channel 204. In use, the mesh 20 is rolled up and placed in the space formed by the channels 202, 204 in a first position in which the open sides of the channels face one another to form a housing or tube. After insertion into the desired location, channel 204 is rotated inside the channel 202 to release the mesh 20.

Referring to FIG. 11, an alternative tool 210 for inserting one of the meshes described comprises an elongate housing 212 around which the mesh is rolled and secured. The tool 210 has means for trapping an edge of the mesh 20 to secure it on the housing of the tool 212, such as a groove 214. In use, once the mesh 20 has been rolled around the housing of the tool 210 it may be secured by a removable clip or other such retaining means (not shown). After insertion of the tool 210 into the desired location, the mesh 20 is released and the tool 210 is rotated to unfurl the mesh 20.

Referring to FIG. 12, another alternative tool 220 for inserting one of the meshes described above in the body comprises two arms 222 pivotally interconnected by a pivot 224. One end of each arm 226 has means for being releasably attached to the mesh 20. The other end of each arm 228 is operable to move the ends that may be attached to the mesh 20 toward or away from one another by rotation around the pivot 224. When the ends of the arms 226,228 to which the mesh 20 can be attached are moved to a position in which they are close to one another, the tool 220 is substantially elongate. Furthermore, the mesh 20 is radially confined by the arms. Once the mesh 20 has been inserted into position, the arms 226,228 can be manipulated to move the ends to which the mesh 20 can be attached apart to unfurl the mesh 20 in its intended position.

Referring to FIG. 13, another tool 230 for inserting one of the meshes described above in its desired location comprises an elongate housing 232 having a number of pairs of holes 234 spaced along its length (in this example three pairs) at the distal end of the tool 230. The housing 232 is hollow and contains a number (in this case three) of pairs of wires 236, made from polypropylene for example, which extend along the length of the housing 232 and out through the pairs of holes 234. The wires 236 also protrude from the proximal end of the housing such that they can be pushed and pulled in and out of the housing 232. The ends of the wires 236 that protrude from the holes 234 have means for releasably attaching to points near the perimeter of the mesh 20.

In use, the wires 236 are attached to the mesh 20 and retracted by pulling them back through the housing 30 such that the mesh 20 is radially confined close to the housing 232. Once the tool 230 has been inserted into the intended position, the wires 236 are pushed into the housing 232 and consequently out through the holes 234 to urge the mesh 20 away from the housing 232. Thus, the mesh 20 can be unfurled in its desired location in the body.

Referring once again to FIG. 5 in order to repair a urethracoele prolapse i.e. a defect in the area A of FIG. 5, the surgeon first locates the defect by examining the patient in the conventional manner. The extent of the defect can then be ascertained and, if necessary, a suitable template used to estimate the shape and dimensions of a preferred surgical implant to repair the defect. A suitably shaped surgical implant can then be selected.

The meshes described above are, in this example, supplied in a single size. After examination of the patient and estimation of the desired dimensions of the preferred mesh, the surgeon cuts the mesh to the preferred size.

Where the mesh comprises a circumferential member 70 the cut made in the mesh is through the transverse members 76 just outward of the circumferential member 70 corresponding most closely with the preferred size of mesh. Thus, regardless of the size to which the mesh is to be cut, a circumferential member 70 defines the perimeter of the mesh, and the perimeter of the mesh is substantially smooth. This desirably reduces the likelihood of infection or edge erosion once the mesh is inserted in the body.

The surgeon then attaches the mesh to or inserts the mesh with one of the insertion tools described herein. For example, the mesh is rolled up and placed within the insertion tool 200 illustrated in FIG. 10, wrapped around the insertion tool 210 illustrated in FIG. 11, attached to the ends of the arms 222 of the insertion tool 220 illustrated in FIG. 12 or attached to the ends of the wires 236 of the insertion tool 230 illustrated in FIG. 13.

An incision 9 is then made in the vaginal wall 12 at the forward most portion of the vaginal wall 12 adjacent the opening of the vaginal cavity. A cutting implement (not illustrated), such as scissors or a specialised cutting tool, is/are then inserted through the incision 9 into the area A, i.e. the lower portion of the anterior vaginal wall 12. Using the cutting implement, a cut is made in the area A parallel with the surface of the vaginal wall 12. In other words, a space is opened up in the vaginal wall 12 over the area of the defect in the vaginal wall 12. The cutting implement is then withdrawn and the mesh 20 is inserted in the space defined by the cut.

Where the insertion tool 200 illustrated in FIG. 10 is used, the tool 200 is inserted into the area A and the channel 202 rotated to a position within the channel 204 to release the mesh 20. The insertion tool 200 can then be retracted and the mesh unfurls due to its inherent resilience or flat memory. Should it be required to help the mesh 20 to unfurl, or slightly re-position the mesh 20 defect 2, an elongate tool (not shown) may be inserted through the incision 9 or needles may be introduced directly through the vaginal wall 12 to manipulate the mesh 20. This procedure can be viewed laproscopically through the incision 9 if desired.

Where the insertion tool 210 illustrated in FIG. 11 is used, it is desirable for the insertion tool 210 to be inserted to one side of the space defined by the cut. The mesh 20 is then released and a needle inserted through the vaginal wall to hold the released edge of the mesh 20 in position. The tool 210 is then rolled across the space defined by the cut in an arc having a centre of rotation around the incision 9. Thus, the mesh 20 is unfurled, but no significant movement is required around the incision 9.

Where the insertion tool 220 illustrated in FIG. 12 is used, the insertion tool 220 is simply inserted through the incision 9 and opened to expand the mesh 20 into its desired location. The mesh 20 is released from the insertion tool 220 which can then be closed and withdrawn through the incision 9.

Finally, where the insertion tool 250 illustrated in FIG. 13 is used, the mesh 20 is retracted by withdrawing the wires 236 through their holes 234 and the mesh is inserted through the incision 9. Once the insertion tool 230 has been inserted into its desired location, the wires 236 are urged forward and out through the holes 234 to expand the mesh in its intended position. The wires 236 can then be released from the mesh 20, withdrawn into the housing 232 and the tool 230 withdrawn through the incision 9.

Once the mesh 20 is in place, the incision may be closed.

However, it can be desirable to secure the 20 in place, rather than rely on the mesh 20 remaining in its desired location of its own accord. In one example, sutures are therefore be placed either laproscopically through the incision 9 or directly through the vaginal wall 12 to hold the mesh 20 in place. In another example, glue capsules provided on the mesh 20 dissolve to secure the mesh 20 to the tissue surrounding the space defined by the cut, or such capsules may be punctured by needles inserted directly through the vaginal wall 12.

The surgical implant described herein is advantageous over the meshes of the prior art in several ways.

In particular the mesh of the present invention includes smoother edges, the polyester material of the present invention being softer than polypropylene. Further, the filaments of the present invention are narrower in diameter enabling them to be more pliable than the strands of the meshes of the prior art. This causes the edge or edges of the mesh of the present invention to have fewer jagged edges and thus be smoother that the edges of meshes or the prior art.

In addition encasement of the mesh in an absorbable coating further protects the tissue both during placement and for a period of time after placement of the surgical implant.

Dual Phase Technology™ such as encasement in an absorbable coating or as otherwise discussed herein provides the implant with good handling characteristics, further it enables the implant to be more easily cut. As described above an absorbable coating may protect the tissues around where the implant is to be located both during placement and for a period of time following placement of the implant in the tissue.

Dual Phase Technology™ may also provide the implant with memory. This memory may allow the implant to be more easily placed flat on the tissue. Further the dual phase technology such as an absorbable coating may provide the implant with mild adhesive properties or tackiness which would aid both the locating and securing of the implant in the tissue.

The surgical implant described herein thus allows tension free repair of hernias, particular vaginal prolapse, with minimum pain. This allows the procedure to be performed under local anaesthetic in an out patient or office setting.

Whilst the above embodiments of the invention have been described with reference to vaginal prolapse, the mesh and surgical tools may equally be used to repair any bodily hernia. Furthermore, whilst the above procedure has been described in relation to a urethrocoele prolapse, prolapse in other parts of the vaginal wall 12 can be treated through incisions elsewhere in the vaginal wall, or other bodily hernias through suitable incisions in the appropriate tissue.

The invention claimed is:

1. A surgical implant configured to be implanted in a body of a patient to treat a vaginal prolapse in the patient, the surgical implant consisting of non-absorbable material to be implanted in the body of the patient and including a knitted mesh having a mass density of less than 25 g/m², with the knitted mesh comprising polypropylene strands having a diameter of less than about 600 μm, major spaces located between adjacent ones of the strands, the major spaces having a width of from about 1 mm to 10 mm, and pores located within the strands, the pores having a diameter of from about 50 μm to 200 μm;

wherein the vaginal prolapse is selected from the group consisting of urethrocoele prolapse, cystocoele prolapse, vault prolapse, uterine prolapse, enterocoele prolapse, and rectocoele prolapse, and wherein the knitted mesh is configured to be secured in place to treat the prolapse.

2. The implant of claim 1, wherein the polypropylene strands are arranged in a pattern that forms a regular network of the major spaces in which each adjacent one of the major spaces has a substantially similar size and shape.

3. The implant of claim 1, wherein the polypropylene strands are arranged to form a regular network of the major spaces, with the regular network of the major spaces characterized by a regular spacing of the major spaces, and the regular spacing of the major spaces is the width of the major spaces.

4. The implant of claim 1, wherein the major spaces have a length, and the length of the major spaces is substantially the same as the width of the major spaces.

5. The implant of claim 1, wherein the major spaces are arranged to form a regular network of the major spaces having a pattern of a regular spacing, with the regular spacing measured between a first location where one strand of the strands intersects a first strand to a second location where the one strand intersects a next nearest second strand.

6. The implant of claim 1, wherein the major spaces are spaced apart to form a pattern having a regular spacing characterized by the width of the major spaces, with the width of the major spaces measured between a first location where one strand of the strands intersects a first strand to a second location where the one strand intersects a next nearest second strand.

7. The implant of claim 1, wherein the major spaces are arranged in a diamond net pattern that forms a regular network of the major spaces, and each of the major spaces has a substantially similar area.

8. The implant of claim 1, wherein the strands are arranged to form a regular network of the major spaces, with the regular network of the major spaces forming a diamond net pattern having a regular spacing between points where the strands interact with each other.

9. The implant of claim 1, wherein the polypropylene strands are formed from at least one biocompatible monofilament, and the major spaces are spaced apart to form a pattern having a regular spacing, with the regular spacing measured between a first location where one strand of the strands intersects a first strand to a second location where the one strand intersects a next nearest second strand, and the regular spacing is characterized by an absence of the at least one biocompatible monofilament in the spacing of the regular network of the major spaces.

10. The implant of claim 1, wherein no portion of the implant is configured to be absorbed by a body of the patient at the time the implant is inserted into the body of the patient for placement at a desired location to treat the vaginal prolapse.

11. The implant of claim 1, wherein the implant has no absorbable coating or encasement.

* * * * *